(12) United States Patent
Marom et al.

(10) Patent No.: US 8,410,176 B2
(45) Date of Patent: Apr. 2, 2013

(54) INTERMEDIATE COMPOUNDS AND PROCESSES FOR THE PREPARATION OF TAPENTADOL AND RELATED COMPOUNDS

(75) Inventors: Ehud Marom, Kfar Saba (IL); Michael Mizhiritskii, Rehovot (IL)

(73) Assignee: Mapi Pharma Ltd., Ness Ziona (IL)

( * ) Notice: Subject to any disclaimer, the term of this patent is extended or adjusted under 35 U.S.C. 154(b) by 0 days.

(21) Appl. No.: 13/520,023

(22) PCT Filed: Dec. 26, 2010

(86) PCT No.: PCT/IL2010/001085

§ 371 (c)(1),
(2), (4) Date: Jun. 29, 2012

(87) PCT Pub. No.: WO2011/080736

PCT Pub. Date: Jul. 7, 2011

(65) Prior Publication Data

US 2012/0283463 A1 Nov. 8, 2012

Related U.S. Application Data

(60) Provisional application No. 61/290,532, filed on Dec. 29, 2009.

(51) Int. Cl.
*A61K 31/137* (2006.01)
*C07F 9/28* (2006.01)
*C07C 211/27* (2006.01)
*C07C 215/54* (2006.01)

(52) U.S. Cl. ........... 514/649; 558/70; 564/336; 564/161

(58) Field of Classification Search .................. 514/649; 564/336, 161; 558/70
See application file for complete search history.

(56) References Cited

U.S. PATENT DOCUMENTS

| | | | |
|---|---|---|---|
| 4,021,224 A | 5/1977 | Pallos et al. | |
| 4,151,172 A | 4/1979 | Ondetti et al. | |
| 4,568,782 A | 2/1986 | Pagnotta et al. | |
| 6,028,087 A | 2/2000 | Bondinell et al. | |
| 2002/0002200 A1 | 1/2002 | Nag et al. | |
| 2002/0037923 A1 | 3/2002 | Travis | |
| 2004/0266732 A1 | 12/2004 | Galvez et al. | |
| 2008/0139585 A1 | 6/2008 | Rathinavelu et al. | |
| 2009/0143397 A1 | 6/2009 | Kuo et al. | |
| 2009/0247764 A1 | 10/2009 | Sundermeier et al. | |
| 2010/0099916 A1* | 4/2010 | Hell et al. ..................... | 564/355 |

FOREIGN PATENT DOCUMENTS

| | | |
|---|---|---|
| CN | 1114321 A | 1/1996 |
| CN | 101486666 A | 7/2009 |
| DE | 4131038 A1 | 4/1993 |
| DE | 4421730 C1 | 11/1995 |
| DE | 19647582 A1 | 5/1998 |
| EP | 0183177 A1 | 6/1986 |
| EP | 0307762 A1 | 3/1989 |
| EP | 0373909 A2 | 6/1990 |
| EP | 0411664 A2 | 2/1991 |
| EP | 0693475 A1 | 1/1996 |
| EP | 0962434 A1 | 12/1999 |
| EP | 0976744 A1 | 2/2000 |
| FR | 2844791 A1 | 3/2004 |
| FR | 2861726 A1 | 5/2005 |
| GB | 2104931 A | 3/1983 |
| GB | 2209943 A | 6/1989 |
| JP | 59098075 A | 6/1984 |
| JP | 04011542 B2 | 2/1992 |
| JP | 05279330 A | 10/1993 |
| JP | 07252264 A | 10/1995 |
| JP | 08027125 A | 1/1996 |
| WO | 91/16892 A1 | 11/1991 |
| WO | 93/22287 | 11/1993 |
| WO | 98/00375 | 1/1998 |
| WO | 99/10343 A1 | 3/1999 |
| WO | 99/20589 A1 | 4/1999 |
| WO | 00/56303 A2 | 9/2000 |
| WO | 01/56382 A1 | 8/2001 |
| WO | 2004/058747 A1 | 7/2004 |
| WO | 2004/108658 | 12/2004 |
| WO | 2005/000788 | 1/2005 |
| WO | 2005/016001 | 2/2005 |
| WO | 2005/068478 A1 | 7/2005 |
| WO | 2006/007794 | 1/2006 |
| WO | 2006/046023 A1 | 5/2006 |
| WO | 2007/003962 A2 | 1/2007 |
| WO | 2007/044796 A2 | 4/2007 |
| WO | 2007/110801 A2 | 10/2007 |
| WO | 2007/111994 A2 | 10/2007 |
| WO | 2008/012047 A1 | 1/2008 |
| WO | 2008/012283 A1 | 1/2008 |
| WO | 2008/028314 | 3/2008 |
| WO | 2008/057859 A2 | 5/2008 |
| WO | 2008/060949 A2 | 5/2008 |

(Continued)

OTHER PUBLICATIONS

Achiwa, Kazuo (1978) Homogeneous catalytic asymmetric hydrogenation of (Z)-2-acetamido-3-methyl-fumaric acid ester, a tetrasubstituted olefin. Tetrahedron Lett. (29):2583-2584.

Bartlett, Paul A. et al., (1982) α-Diazophosphonic acids as potential photoaffinity labeling reagents: synthesis, stability, and photochemistry. J Org Chem 47(7):1284-1291.

Bhattacharya, Alok K. and Thyagarajan, G. (1981) Michaelis-Arbuzov rearrangement. Chem. Rev. 81 (4):415-430.

Flynn, A. B. and Ogilvie, W. W. (2007) Stereocontrolled Synthesis of Tetrasubstituted Olefins. Chem. Rev. 107 (11):4698-4745.

(Continued)

*Primary Examiner* — Kristin Bianchi
(74) *Attorney, Agent, or Firm* — Rothwell, Figg, Ernst & Manbeck, P.C.

(57) ABSTRACT

The present invention discloses processes for the preparation of 3-[(1R,2R)-3-(dimethyl-amino)-1-ethyl-2-methyl-propyl] phenol (Tapentadol), salts thereof and related compounds of formula (A), including stereoisomers and pharmaceutically acceptable salts thereof, and to certain intermediates used in such process.

25 Claims, No Drawings

FOREIGN PATENT DOCUMENTS

| WO | 2008/144933 A1 | 12/2008 |
|---|---|---|
| WO | 2009/040285 | 4/2009 |
| WO | 2009/045479 A1 | 4/2009 |
| WO | 2009/136889 A1 | 11/2009 |
| WO | 2010/039815 A1 | 4/2010 |
| WO | 2010/111504 A2 | 9/2010 |

OTHER PUBLICATIONS

Hayashi, Tamio et al., (1988) Catalytic asymmetric hydrogenation of β-disubstituted α-phenylacrylic acids asymmetric synthesis of carboxylic acids containing two vicinal chiral carbon centers.Tetrahedron Lett 29 (46):5969-5972.

Muller, E. (ed.) Methoden der Organishen Chemie (Houben-Weyl); George Theime Verlag: Stuttgart, 1964, vol. 12/1, p. 446.

Patois,Carl et al., Bis(Trifluoroethyl)(Carboethoxymethyl)Phosphonate [Acetic acid, [bis(2,2,2-trifluoroethoxy)phosphinyl]-, ethyl ester] Organic Syntheses, Coll. vol. 9, p. 88 (1998); vol. 73, p. 152 (1996).

Sano, Shigeki et al., (1997) New reaction mode of the Horner-Wadsworth-Emmons reaction using $Sn(OSO_2CF_3)_2$ and N-ethylpiperidine. Chem. Commun. 6: 559-560.

Sano, Shigeki et al., (1998) New Reaction Mode of the Horner-Wadsworth-Emmons Reaction for the Preparation of α-Fluoro-α,β-unsaturated Esters. Synlett 7:777-779.

Sano, Shigeki et al., (2002) Enantioselective Horner-Wadsworth-Emmons reaction for the asymmetric synthesis of α-fluoro-α,β-unsaturated esters. Tetrahedron Lett., 43(2):281-284.

Sano, Shigeki et al., (2002) A Facile Method for the Stereoselective Horner-Wadsworth-Emmons Reaction of Aryl Alkyl Ketones. Chem. Pharm. Bull., 50(5):706-709.

Sano, Shigeki et al., (2002) Stereoselective Synthesis of Tetrasubstituted (Z)-Alkenes from Aryl Alkyl Ketones Utilizing the Horner-Wadsworth-Emmons Reaction. Chem. Pharm. Bull. 50(9):1300-1302.

Sano, Shigeki et al., (2003) (E)-Selective Homer-Wadsworth-Emmons reaction of aldehydes with bis-(2,2,2-trifluoroethyl)phosphonoacetic acid ARKIVOC 2003 (viii) 93-101.

Seebach, Dieter et al., Chiral media for asymmetric solvent inductions. (s,s)-(+)-1,4-bis(dimethylamino)-2,3-dimethoxybutane from (r,r)-(+)-diethyl tartrate. Organic Syntheses, Coll. vol. 7, p. 41 (1990); vol. 61, p. 24 (1983), 11 pages.

Shindo, Mitsuru and Mori, Seiji (2008) Torquoselective Olefination of Carbonyl Compounds with Ynolates: Highly Efficient Stereoselective Synthesis of Tetrasubstituted Alkenes. SYNLET 15:2231-2243.

Smith, Amos B. et al., (2005) Preparation of [1-(methoxymethylcarbamoyl)ethyl] phosphonic acid bis-(2,2,2-trifluoroethyl) ester: a useful intermediate in the synthesis of z-unsaturated n-methoxy-n-methylamides. Organic Syntheses 82:147, 8 pages.

Still, W. Clark and Gennari, Cesare (1983) Direct synthesis of Z-unsaturated esters. A useful modification of the horner-emmons olefination. Tetrahedron Lett. 24(41):4405-4408.

Tang, Wenjun and Zhang, Xumu (2003) New Chiral Phosphorus Ligands for Enantioselective Hydrogenation. Chem. Rev. 103(8):3029-3070.

Tang, Wenjun et al., (2003) Enantioselective Hydrogenation of Tetrasubstituted Olefins of Cyclic β-(Acylamino) acrylates. J. Am. Chem. Soc. 125(32):9570-9571.

Timperley, Christopher M.et al., (2002) Fluorinated phosphorus compounds: Part 6. The synthesis of bis(fluoroalkyl) phosphites and bis(fluoroalkyl) phosphorohalidates. J. Fluorine Chem. 113(1):65-78.

Wustenberg, Bettina and Pfaltz, Andreas (2008) Homogeneous Hydrogenation of Tri- and Tetrasubstituted Olefins: Comparison of Iridium-Phospinooxazoline [Ir-PHOX] Complexes and Crabtree Catalysts with Hexafluorophosphate (PF6) and Tetrakis[3,5-bis(trifluoromethyl)phenyl]borate (BArF) as Counterions. Adv. Synth. Catal. 350(1):174-178.

International Search Report and Written Opinion of PCT/IL10/01085 dated May 4, 2011, 8 pages.

* cited by examiner

INTERMEDIATE COMPOUNDS AND PROCESSES FOR THE PREPARATION OF TAPENTADOL AND RELATED COMPOUNDS

CROSS REFERENCE TO RELATED APPLICATIONS

This application is a 35 U.S.C. §371 National Phase Entry Application from PCT/IL2010/001085, filed Dec. 26, 2010, and designating the United States and claims priority to U.S. Application No. 61/290,532 filed Dec. 29, 2009, which are incorporated herein in their entireties.

FIELD OF THE INVENTION

The present invention relates to a process for the preparation of 3-[(1R,2R)-3-(dimethyl-amino)-1-ethyl-2-methylpropyl]phenol hydrochloride (Tapentadol) and related compounds of formula (A), and to certain intermediates formed in such processes.

BACKGROUND OF THE INVENTION

The pain management market is segmented according to the severity of the pain being treated.
- Mild pain (e.g. headache) is generally treated with over-the-counter drugs, such as aspirin.
- Moderate pain (e.g. arthritis) is often treated with weak opioids such as codeine or hydrocodone that require a prescription, generally from a general practitioner.
- Severe pain (e.g. cancer pain, chronic back pain) is treated with strong opioids such as morphine, oxycodone or fentanyl, which also require a prescription, often provided by a specialist.

While opioids continue to remain the gold standard in pain relief, they have well 25 recognized shortcomings.
- significant adverse side effects—e.g. respiratory depression, nausea, vomiting, dizziness, sedation, constipation;
- tolerance—chronic sufferers often develop tolerance to opioids and require a stronger dose to achieve effective pain relief, concomitantly increasing the level of side effects;
- dependency—concerns about addiction may influence clinicians to prescribe less than adequate doses; and
- potential for abuse—recreational use.

Tapentadol hydrochloride is an oral drug for the relief of moderate to severe acute pain. Tapentadol assumes a special position amongst centrally-acting analgesics, since this active ingredient gives rise to a pronounced inhibition of pain without the side effects which are known for opioids.

Currently available pharmacological treatment of pain includes the following analgesics: non-steroidal anti-inflammatory drugs (NSAIDs), cyclo-oxygenase II (COX-II) inhibitors, acetaminophen and opioids. Notwithstanding the numerous available analgesic medications, 60% to 80% of patients suffering from chronic pain are currently treated inadequately. Tapentadol helps fill the gap for those subjects whose pain cannot be effectively controlled by existing medications.

Tapentadol acts in two ways, opioid (narcotic) and non-opioid. It has a unique pharmacological profile with two postulated mechanisms of action, combining μ-opioid receptor agonism and norepinephrine reuptake inhibition in a single molecule. It is being developed in immediate-release and extended-release formulations.

The chemical structure of tapentadol (1) has been disclosed in EP-A-0693475 as compound (+21). The synthesis of tapentadol is described in Example 1 and Example 24 steps 1 to 3 and is outlined below (Scheme 1):

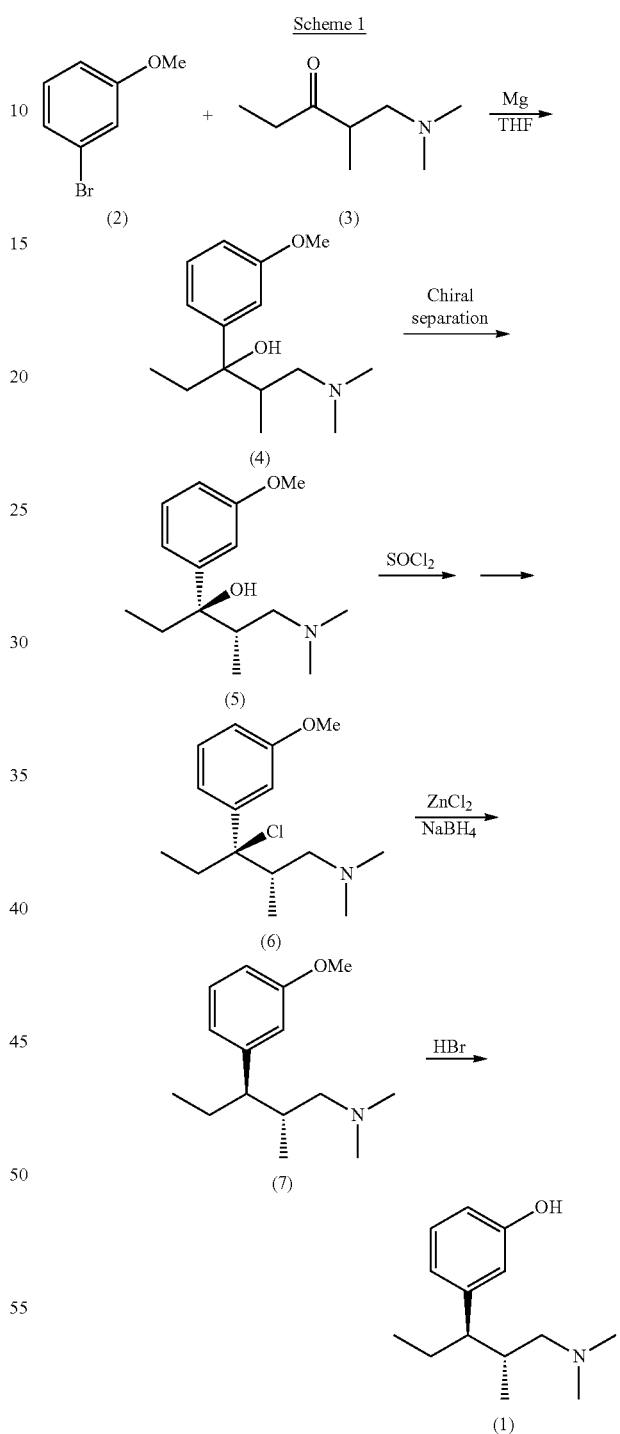

The synthetic precursor of tapentadol in the above scheme is (2R,3R)-3-(3-methoxy-phenyl)-N,N,2-trimethylpentanamine (7) which can be obtained by removing the tertiary hydroxy group of (2S,3R)-1-(dimethylamino)-3-(3-methoxyphenyl)-2-methyl-3-pentanol (5) by consecutive conversion into the corresponding halogenide (6) with thionyl chloride and subsequent removal of the Cl by treatment with zinc borohydride, zinc cyanoborohydride and/or tin cyanoborohydride. This procedure has the disadvantage that the halogenide compound is prepared using an excess amount of thionyl chloride which is an aggressive chlorinating agent. Moreover the hydrogenation reagents such as zinc borohydride, zinc cyanoborohydride and tin cyanoborohydride present a considerable fire and health danger when used on an industrial scale. The main disadvantage, however, is the usage of column chiral chromatography for the separation of the stereoisomers.

WO 2004/108658 discloses an alternative process for obtaining (2R,3R)-3-(3-methoxy-phenyl)-N,N,2-trimethyl-pentanamine (1) by converting (2S,3S)-1-(dimethylamino)-3-(3-methoxyphenyl)-2-methyl-3-pentenol (9) into a mixture of (2R,3R) (7) and (2R,3S)-3-(3-methoxyphenyl)-N,N,2-trimethylpentanamine (10) as outlined below (Scheme 2).

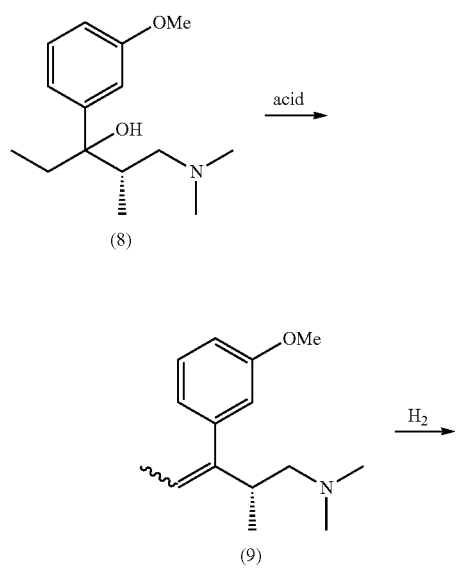

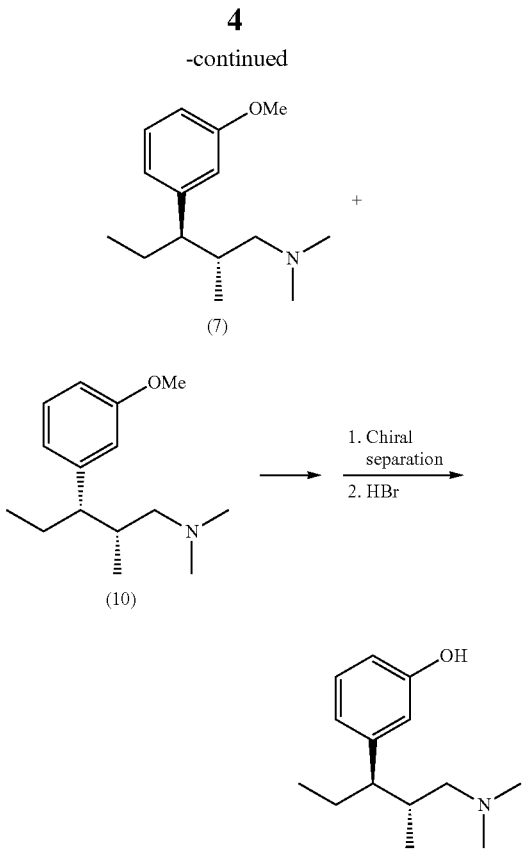

The resulting mixture of (2R,3R) and (2R,3S)-3-(3-methoxyphenyl)-N,N,2-trimethyl-pentanamine is then separated into its individual stereoisomers (7) and (10) in order to obtain the desired (2R,3R)-3-(3-methoxyphenyl)-N,N,2-trimethyl-pentan-amine (7), which can then be converted into tapentadol by e.g. heating with concentrated hydrobromic acid as described in EP-A-0693475.

WO 2005/000788 discloses an alternative process for obtaining (2R,3R)-3-(3-methoxy-phenyl)-N,N,2-trimethyl-pentanamine by converting (2S,3S)-1-(dimethylamino)-3-(3-methoxyphenyl)-2-methyl-3-pentanol into a mixture of (2R,3R) and (2R,3S)-3-(3-methoxyphenyl)-N,N,2-trimethylpentanamine as outlined below.

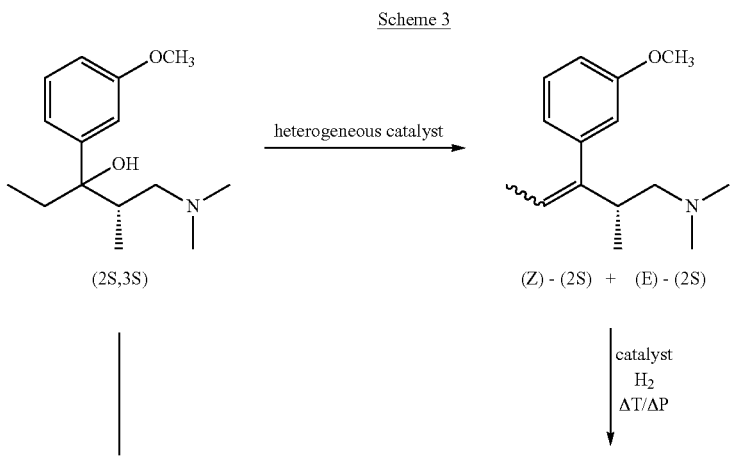

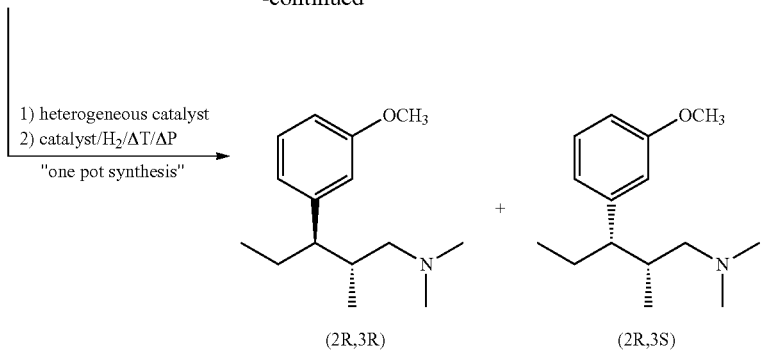

Both processes of WO 2004/108658 and WO 2005/000788 have the disadvantage that [3-(3-methoxyphenyl)-N,N,2-trimethylpentanamine is obtained as a mixture of the (2R,3R) and (2R,3S) stereoisomers which have to be separated in order to obtain the desired (2R,3R) stereoisomer. The undesired (2R,3S) stereoisomer cannot be converted into the desired (2R,3R) stereoisomer and has to be disposed of as chemical waste, which is economically undesirable for any industrial scale production.

WO 2008/012047 discloses yet another method for preparation of tapentadol, starting from 1-(3-methoxyphenyl)propan-1-one (Scheme 4):

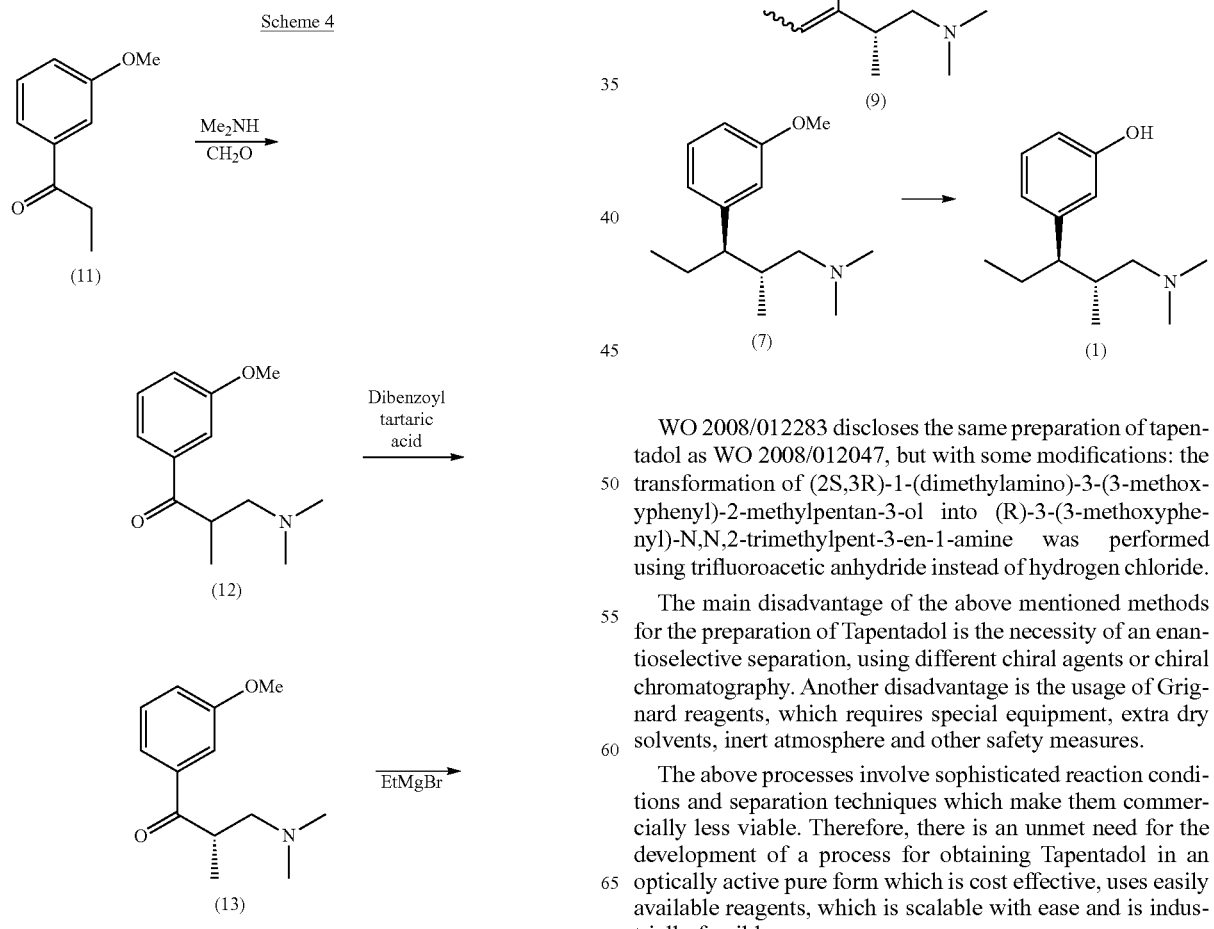

WO 2008/012283 discloses the same preparation of tapentadol as WO 2008/012047, but with some modifications: the transformation of (2S,3R)-1-(dimethylamino)-3-(3-methoxyphenyl)-2-methylpentan-3-ol into (R)-3-(3-methoxyphenyl)-N,N,2-trimethylpent-3-en-1-amine was performed using trifluoroacetic anhydride instead of hydrogen chloride.

The main disadvantage of the above mentioned methods for the preparation of Tapentadol is the necessity of an enantioselective separation, using different chiral agents or chiral chromatography. Another disadvantage is the usage of Grignard reagents, which requires special equipment, extra dry solvents, inert atmosphere and other safety measures.

The above processes involve sophisticated reaction conditions and separation techniques which make them commercially less viable. Therefore, there is an unmet need for the development of a process for obtaining Tapentadol in an optically active pure form which is cost effective, uses easily available reagents, which is scalable with ease and is industrially feasible.

SUMMARY OF THE INVENTION

The present invention discloses processes for the preparation of 3-[(1R,2R)-3-(dimethyl-amino)-1-ethyl-2-methyl-propyl]phenol hydrochloride (Tapentadol) and related compounds of formula (A), including stereoisomers and pharmaceutically acceptable salts thereof, and to certain intermediates used in such process. The process of the invention avoids the disadvantages of the prior art processes, in that it avoids the problematic enantioselective separation step, uses only safe and inexpensive reagents and steps, and can easily be performed on an industrial scale. According to one embodiment, the present invention provides a process for the preparation of a compound of formula (A):

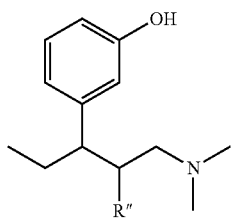

(A)

or stereoisomers, pharmaceutically acceptable salts or combination thereof, comprising the steps (a), (b1), (c1), (d) and (e); or (a), (b2), (c2), (d) and (e):

a) a Horner-Wadsworth-Emmons (HWE) reaction between 1-(3-methoxy-phenyl)-propan-1-one and a phosphonate compound of formula (I) to obtain a compound of formula (II):

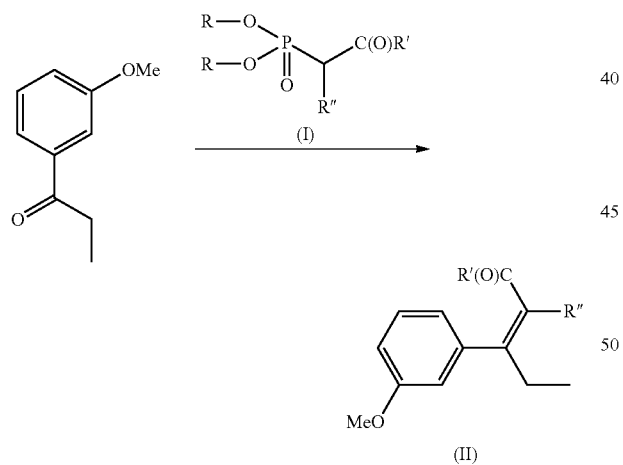

wherein each R is independently alkyl or aryl which is optionally substituted with an electron withdrawing group, preferably R is 2,2,2-trifluoroethyl, phenyl or o-tolyl;

R' is (i) —$NR^1R^2$ wherein $R^1$ and $R^2$ are each alkyl; (ii) —$OR^3$ wherein $R^3$ is alkyl, aryl or alkylaryl; or (iii) a functional group which can be converted to an amine group, preferably an $NMe_2$ group; and R" is H, alkyl, aryl, heteroalkyl, heteroaryl, alkylaryl or cycloalkyl;

b1) and c1) hydrogenating compound (II) to obtain the compound of formula (III):

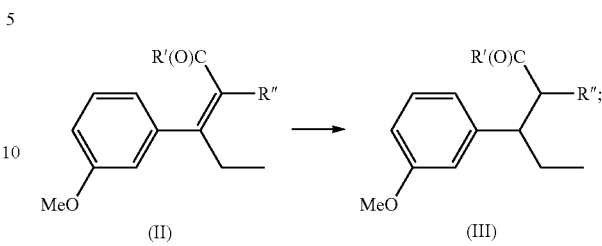

and optionally, when R' is other than $NMe_2$, converting the compound of formula (III) to a compound of formula (IV):

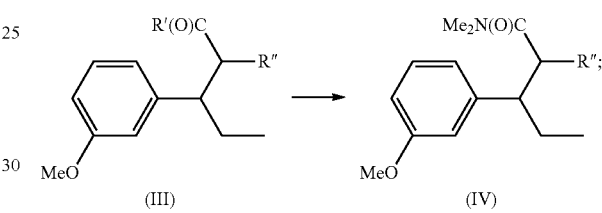

or b2) and c2) optionally, when R' is other than $NMe_2$, converting the compound of formula (II) to a compound of formula (V);

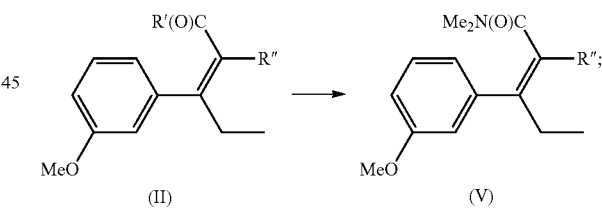

and hydrogenating compound (V) to obtain a compound of formula (IV):

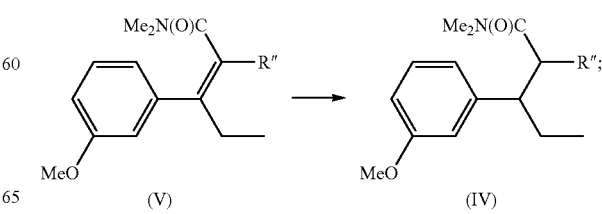

d) reducing the compound of formula (IV) obtained in steps (c1) or (c2) to a compound of formula (VI):

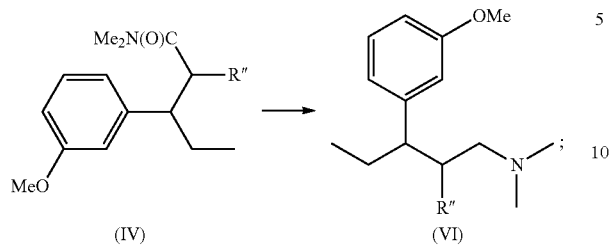

and
e) converting the compound of formula (VI) to a compound of formula (A):

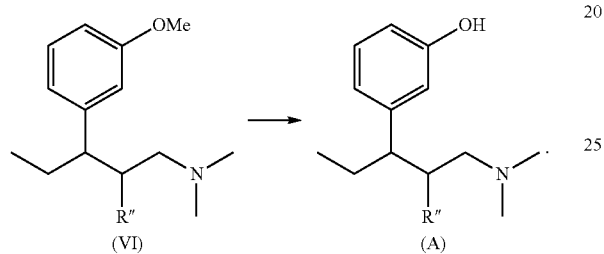

In one embodiment, the process comprises the steps of (a), (b1), (c1), (d) and (e). In another embodiment, the process comprises the steps of (a), (b2), (c2), (d) and (e). In some embodiments, R' is other than NMe$_2$, and step (c1) and (b2) are performed. In other embodiments, however, R' is NMe$_2$, and step (c1) and (b2) are not performed. Each possibility represents a separate embodiment of the present invention.

According to one embodiment, R" is methyl, and the process of the invention produces Tapentadol, or its stereoisomers or pharmaceutically acceptable salts. In accordance with this embodiment, the process comprises the steps (a), (b1), (c1), (d) and (e), or (a), (b2), (c2), (d) and (e):

a) a Horner-Wadsworth-Emmons (HWE) reaction between 1-(3-methoxy-phenyl)-propan-1-one and a phosphonate compound of formula (I-a) to obtain a compound of formula (II-a):

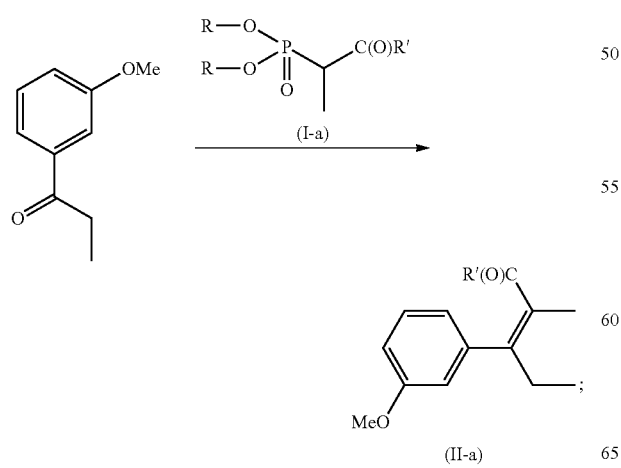

wherein each R is independently alkyl or aryl which is optionally substituted with an electron withdrawing group, preferably R is 2,2,2-trifluoroethyl, phenyl or o-tolyl; and R' is (i) —NR$^1$R$^2$ wherein R$^1$ and R$^2$ are each alkyl; (ii) —OR$^3$ wherein R$^3$ is alkyl, aryl or alkylaryl; or (iii) a functional group which can be converted to an amine group, preferably NMe$_2$ group;

b1) and c1) hydrogenating the compound of formula (II-a) to obtain a compound of formula (III-a):

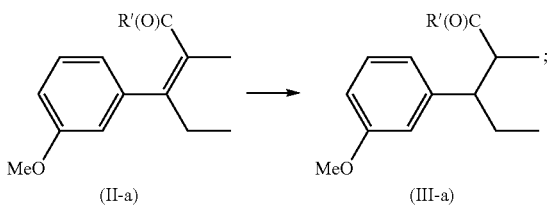

and
optionally, when R' is other than NMe$_2$, converting the compound of formula (III-a) to the compound of formula (IV-a):

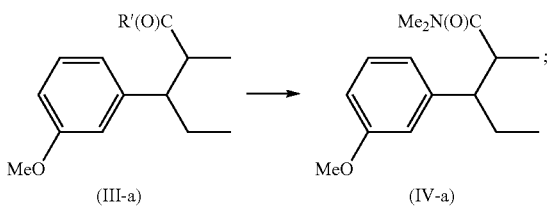

or
b2) and c2) optionally, when R' is other than NMe$_2$, converting the compound of formula (II-a) to a compound of formula (V-a); and

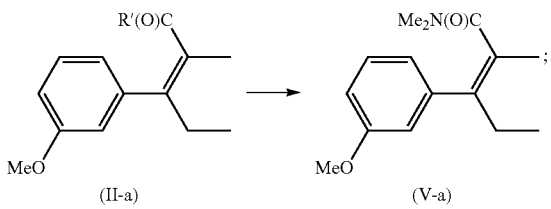

and
hydrogenating compound (V-a) to obtain a compound of formula (IV-a):

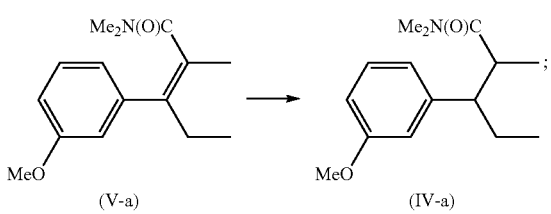

d) reducing the resultant compound of formula (IV-a) obtained by step (c1) or (c2) to 3-(3-methoxyphenyl)-N,N,2-trimethylpentan-1-amine of formula (VI-a):

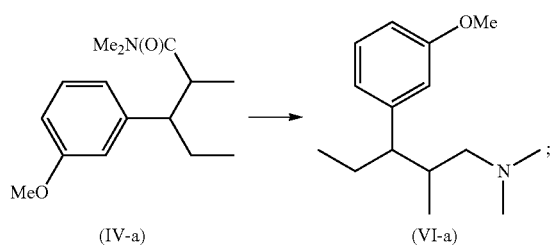

and e) converting 3-(3-methoxyphenyl)-N,N,2-trimethylpentan-1-amine to 3-[3-(dimethylamino)-1-ethyl-2-methylpropyl]phenol or a stereoisomer thereof.

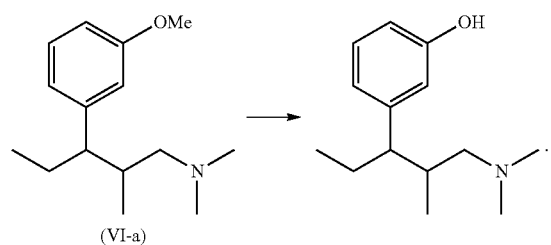

In one currently preferred embodiment, the product of this process is Tapentadol (i.e., 3-[1R,2R)-3-(dimethylamino)-1-ethyl-2-methylpropyl]phenol). In some embodiments, the process for preparing Tapentadol comprises the steps of (a), (b1), (c1), (d) and (e). In another embodiments, the process for preparing Tapentadol comprises the steps of (a), (b2), (c2), (d) and (e). In some embodiments, R' is other than NMe$_2$, and step (e1) and (b2) are performed. In other embodiments, however, R' is NMe$_2$, and step (c1) and (b2) are not performed. Each possibility represents a separate embodiment of the present invention.

In certain embodiments, step (a) of the process of the present invention comprises a Horner-Wadsworth-Emmons (HWE) reaction performed in the presence of at least one additive. In particular embodiments, the additive is a metal trifluoroacetate or a trifluoromethanesulfonate, for example the trifluoromethanesulfonate additive may be Sn(OSO$_2$CF$_3$)$_2$. In additional embodiments, the additive is used in combination with amine, preferably a tertiary amine such as N-ethylpiperidine. In additional embodiments, the additive is selected from an inorganic and organic base. Non-limiting examples of inorganic bases include alkali metal, alkaline earth hydrides, and alcoholates. Each possibility represents a separate embodiment of the invention. In particular embodiments, the alkali metal hydride is sodium hydride. Non-limiting examples of organic bases are tertiary amines including DNU, DBN and diisopropylethylamine. According to the principles of the present invention, the organic base may be used in combination with alkali metal or alkaline earth metal halogenides, for example, lithium chloride or bromide.

The product of step (a), i.e., a compound of formula (II) or (II-a) may be obtained in the form of a Z-isomer, E-isomer or any mixtures thereof. Each possibility represents a separate embodiment of the present invention.

In various embodiments, the step of hydrogenation of the compound of formula (II) to obtain the compound of formula (III) (step b1), or the step of hydrogenation of the corresponding dimethylamide derivative (V) to obtain the compound of formula (IV) (step c2) is carried out in the presence of a catalyst under hydrogen atmosphere in an organic solvent. In particular embodiments, the catalyst is selected from the group consisting of copper, zinc, nickel, ruthenium, palladium, platinum, rhodium, and their oxides. Each possibility represents a separate embodiment of the invention. In additional embodiments, the catalyst is used in combination with supports (e.g., solid and liquid supports), which include silica, alumina, silica-alumina, titania, diatomaceous earth, kaolin, activated carbon, carbon, graphite, zeolite, montmorillonite and the like, clays, and alkaline earth metal silicates. Each possibility represents a separate embodiment of the invention. In some embodiments, the catalyst is Raney nickel. In alternative embodiments the catalyst is Pd/C.

In some embodiments, the step of hydrogenation of the compound of formula (II) to obtain the compound of formula (III) (step b1), or the step of hydrogenation of the corresponding dimethylamide derivative (V) to obtain the compound of formula (IV) (step c2), is carried out with hydrogen pressure of up to about 200 bar, preferably with hydrogen pressure of about 1 to about 200 bar. Alternatively, the hydrogenation is carried out with hydrogen pressure of about 5 to about 40 bar. In another alternative the hydrogenation is carried out with hydrogen pressure of about 50 to about 100 bar.

In certain embodiments, the step of hydrogenation comprises the use of a catalyst selected from the group consisting of complexes of transition metals, including rhodium, ruthenium, iridium, platinum, titanium, zirconium and palladium. Each possibility represents a separate embodiment of the invention. In some embodiments, the catalyst is attached to or associated with a chiral ligand such as a chiral phosphorus ligand.

According to the principles of the present invention, the product of the hydrogenation (i.e., the products of steps (b1) or (c2)), may be obtained in optically active form, preferably the threo-isomer. In other embodiments, the product of the hydrogenation is obtained as a racemic mixture. In other embodiments, the product may be obtained in different diastereomeric mixtures, e.g., the (R,R), (R,S), (S,R) or (S,S) isomers in any ratios. Each possibility represents a separate embodiment of the present invention.

In another embodiment, the reduction of the amide to 3-(3-methoxyphenyl)-N,N,2-trimethylpentan-1-amine (step d) is carried out with a reducing agent. In some embodiments, the reducing agent is selected from the group consisting of borane and its complex with dimethylsulfide, pyridine, triethylamine and the like; lithium and sodium borohydride in the presence of Lewis acid, such as boron trifluoride diethyl ether complex, aluminum-, titanium- or cobalt-chlorides and the like, or in the presence of trimethylchlorosilane or phosphorus oxychloride; or an aluminum hydride such as AlH$_3$ and its complex with amines, LiAlH$_4$, sodium bis(2-methoxyethoxy)aluminium hydride (Red-Al) and diisobutylaluminum hydride. Each possibility represents a separate embodiment of the invention. In particular embodiments, the reducing agent is sodium borohydride in the presence of boron trifluoride diethyl ether complex.

The process of the invention may further comprise the step of converting the compound of formula (A) or its precursor of formula (VI) to its pharmaceutically acceptable salt. For example, when the compound of formula (A) is Tapentadol, the process may comprise the step of converting Tapentadol or its precursor of formula (VI-a) to its pharmaceutically acceptable salt, preferably the hydrochloride salt.

The present invention further relates to certain intermediates produced in the above-described processes. According to a first aspect, the present invention provides a phosphonate compound represented by the structure of formula I-a:

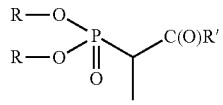

(I-a)

wherein each R is independently alkyl or aryl which is optionally substituted with an electron withdrawing group, preferably wherein R is 2,2,2-trifluoroethyl, phenyl or o-tolyl, and R' is $N(CH_3)_2$.

In one embodiment, the phosphonate compound represented by the structure of formula (I-a) is used for the preparation of compounds with a carbon-carbon double bond, such as but not limited to Tapentadol.

According to a second aspect, the present invention provides a compound represented by the structure of formula (II):

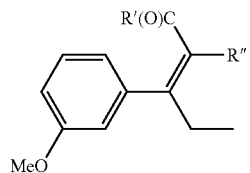

(II)

wherein R' is $—NR^1R^2$ wherein $R^1$ and $R^2$ are each alkyl, preferably wherein $R^1$ and $R^2$ are each methyl; and R" is alkyl, aryl, heteroalkyl, heteroaryl, alkylaryl or cycloalkyl, preferably wherein R" is methyl. In one embodiment, $R^1$ and $R^2$ and R" are each methyl.

In one embodiment this compound exists as Z-isomer. In another embodiment, this compound exists as a mixture of Z- and E-isomers. In one currently preferred embodiment, R" in compound (II) is methyl. In other currently preferred embodiments, R' in formula (II) is $N(CH_3)_2$. Each possibility represents a separate embodiment of the present invention.

According to a third aspect, the present invention provides a compound represented by the structure of formula (III), or a stereoisomer thereof. In some embodiments, this compound exists in optically active form, preferably as a threo-isomer:

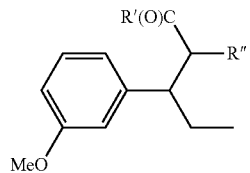

(III)

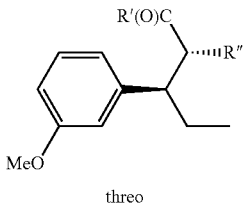

(III)

threo wherein R' is (i) $—NR^1R^2$ wherein $R^1$ and $R^2$ are each alkyl, preferably wherein $R^1$ and $R^2$ are each methyl; (ii) $—OR^3$ wherein $R^3$ is alkyl, aryl or alkylaryl; or (iii) a functional group which can be converted to an amine group, preferably $NMe_2$ group; and R" is alkyl, aryl, heteroalkyl, heteroaryl, alkylaryl or cycloalkyl, preferably wherein R" is methyl.

In some embodiments, this compound exists as a racemic mixture. In one currently preferred embodiment, embodiment, R" in compound (III) is methyl. In other currently preferred embodiments, R' in formula (III) is $N(CH_3)_2$. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

As contemplated herein, the applicants have found a new process, by which Tapentadol and similar compounds of formula (A) may be prepared on a manufacturing scale from the compound of formula (II) in several steps. The process comprises the steps (a), (b1), (e1), (d) and (e), or (a), (b2), (c2), (d) and (e) (wherein steps (e1) and (b2) are optional), as illustrated in Schemes 5-7 below for the preparation of a compound of formula (A), or in Schemes 8-10 below for the preparation of Tapentadol and stereoisomers thereof. The process may result in racemic products, or in products that are optically active, e.g., enantiomerically or diastereomerically enriched or pure.

In general, the process for preparing compound (A) comprises the following steps:

a) a Horner-Wadsworth-Emmons (HWE) reaction between 1-(3-methoxy-phenyl)-propan-1-one and a phosphonate compound of formula (I) to obtain a compound of formula (II);

b1) and c1) hydrogenating compound (II) to obtain the compound of formula (III); and optionally, when R' is other than $NMe_2$, converting the compound of formula (III) to a compound of formula (IV); or b2) and c2) optionally, when R' is other than $NMe_2$, converting the compound of formula (II) to a compound of formula (V); and hydrogenating compound (V) to obtain the compound of formula (IV);

d) reducing the compound of formula (IV) obtained in steps (e1) or (c2) to a compound of formula (VI); and e) converting the compound of formula (VI) to a compound of formula (A).

In one embodiment, the process comprises the steps of (a), (b1), (e1), (d) and (e), as illustrated in Scheme 5 below.

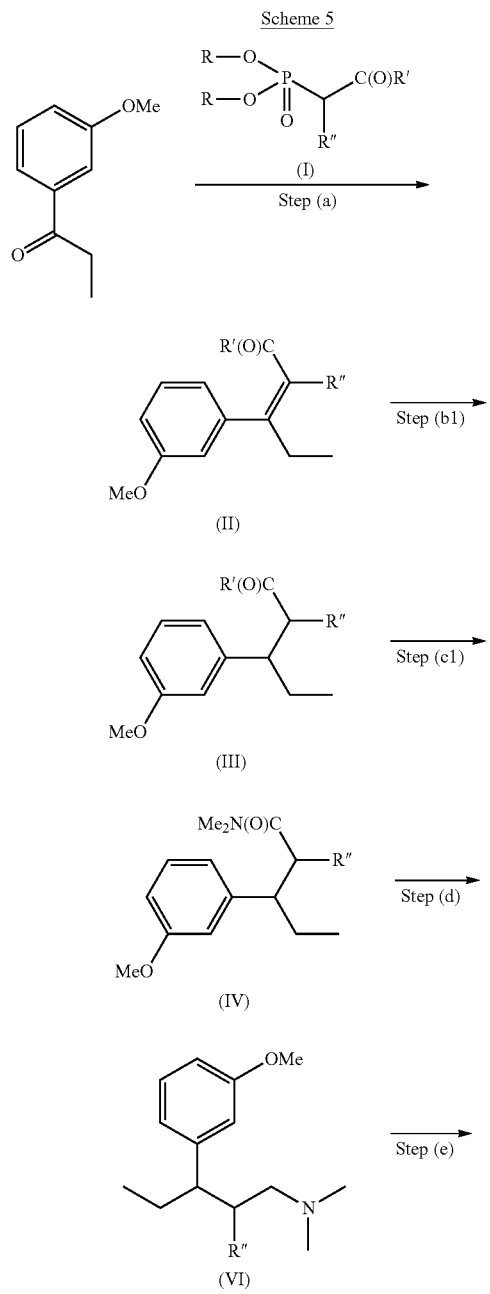

In another embodiment, the process comprises the steps of (a), (b2), (c2), (d) and (e), as illustrated in Scheme 6 below.

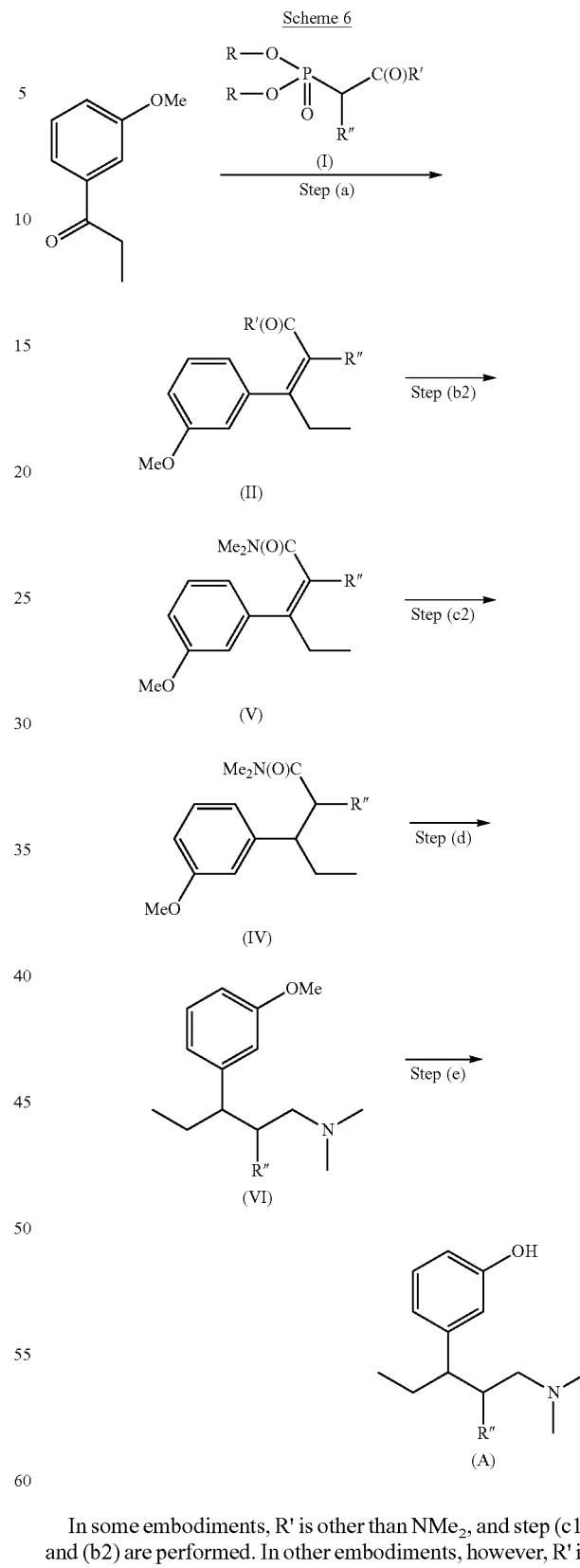

In some embodiments, R' is other than NMe$_2$, and step (c1) and (b2) are performed. In other embodiments, however, R' is NMe$_2$, and step (c1) and (b2) are not performed. In accordance with these embodiments, the process of the invention comprises the steps of (a), (b1), (d) and (e), or (a), (c2), (d) and (e) (Scheme 7):

17

Scheme 7

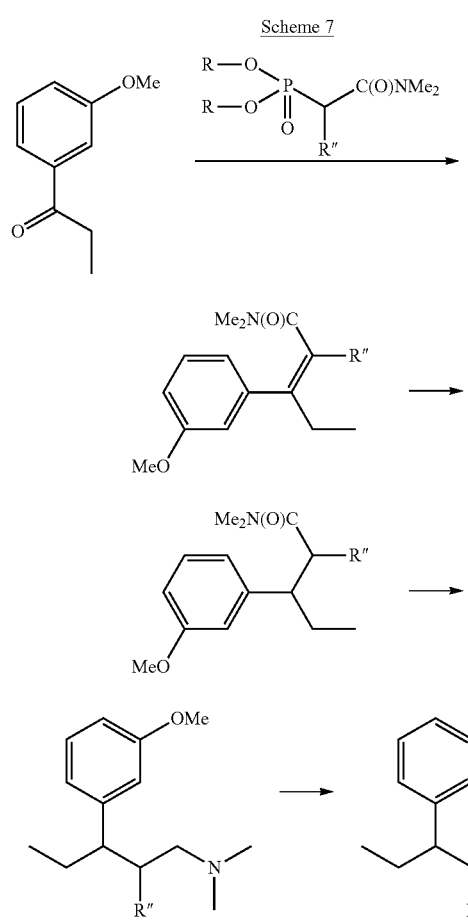

According to another aspect, R″ is methyl. In one particular embodiment, the product of this reaction is 3-[(1R,2R)-3-(dimethylamino)-1-ethyl-2-methylpropyl]phenol (Tapentadol), or stereoisomers or pharmaceutically acceptable salts thereof. In one embodiment, the process for preparing Tapentadol or stereoisomers thereof comprises the steps of (a), (b1), (c1), (d) and (e), as illustrated in Scheme 8 below.

Scheme 8

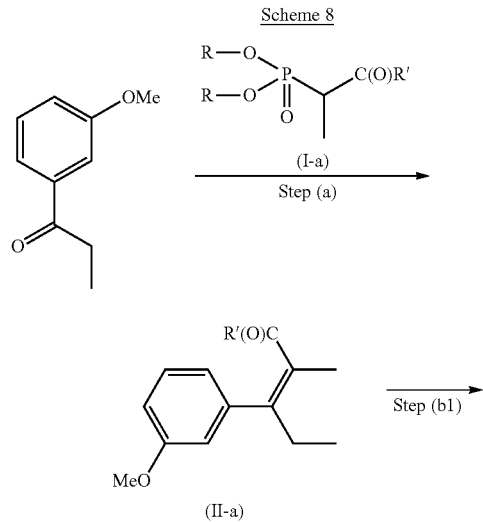

18

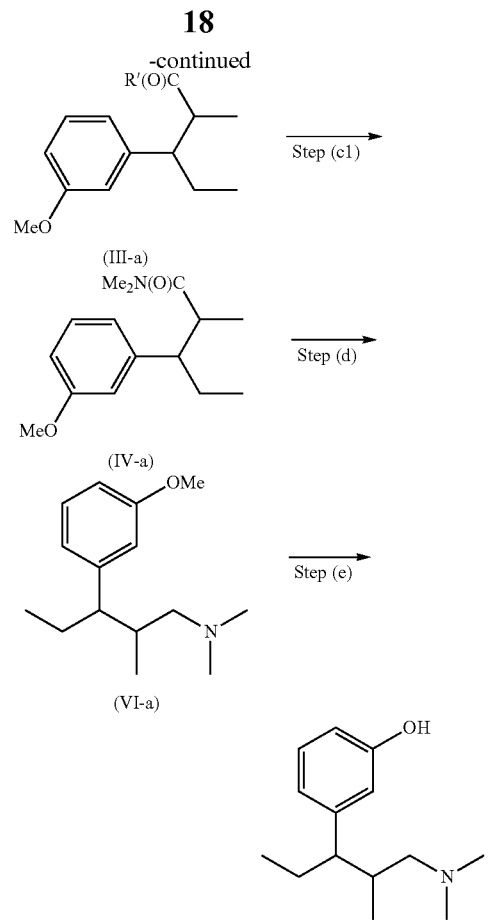

In another embodiment, the process for preparing Tapentadol or stereoisomers thereof comprises the steps of (a), (b2), (c2), (d) and (e), as illustrated in Scheme 9 below.

Scheme 9

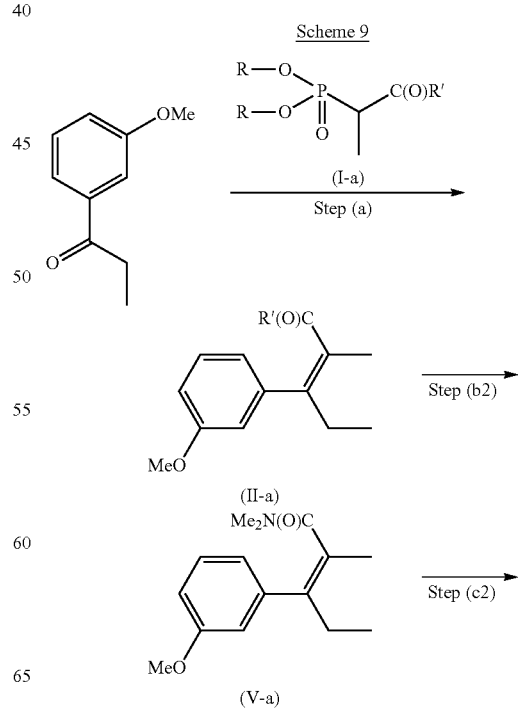

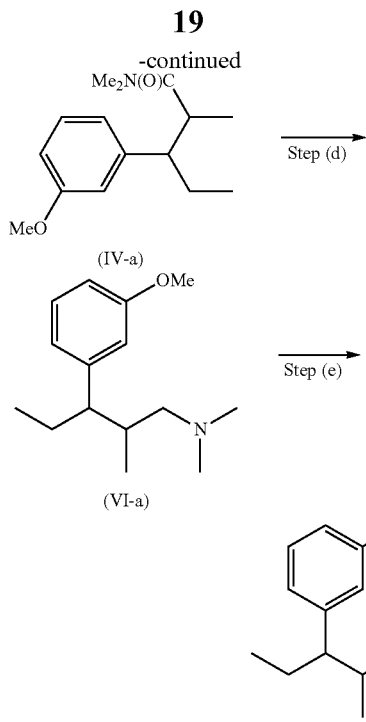

In some embodiments, R' is other than NMe$_2$, and step (c1) and (b2) are performed. In other embodiments, however, R' is NMe$_2$, and step (c1) and (b2) are not performed. In accordance with these embodiments, the process of the invention comprises the steps of (a), (b1), (d) and (e), or (a), (c2), (d) and (e) (Scheme 10):

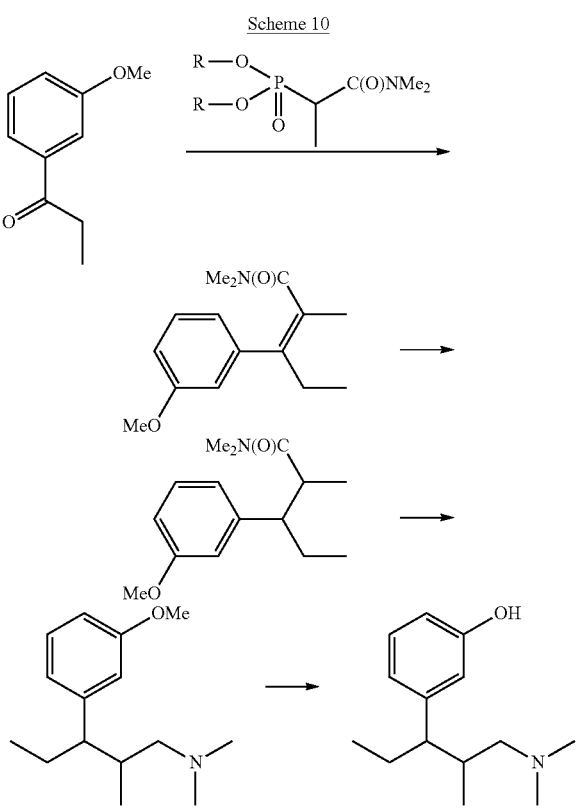

Each possibility represents a separate embodiment of the present invention. It is understood that said process may be used to prepare racemic compounds as well as optically active compounds such as Tapentadol.

In one embodiment, the process of the invention can be used to prepare a compound of formula (A) in optically active form:

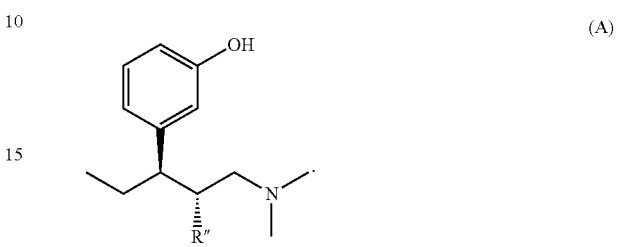

In another embodiment the process of the invention can be used to prepare Tapentadol in an optically active form. The process comprises the following steps:

a) a Horner-Wadsworth-Emmons (HWE) reaction between 1-(3-methoxy-phenyl)-propan-1-one and a phosphonate compound of formula (I-a) to obtain a compound of formula (II-a):

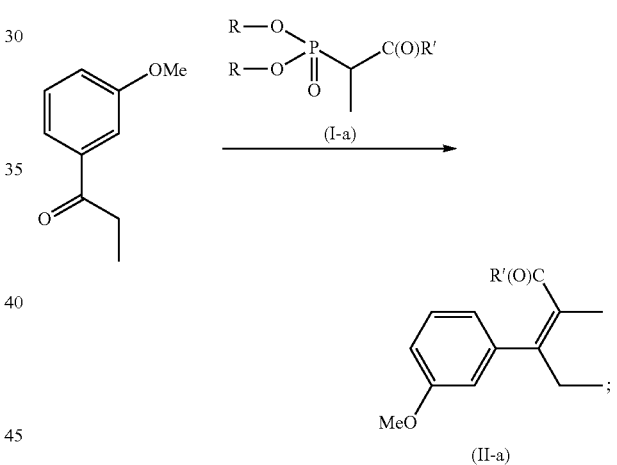

wherein R and R' are as defined above, b1) and c1) hydrogenating the compound of formula (II-a) in the presence of a chiral catalyst to obtain a compound of formula (III-a):

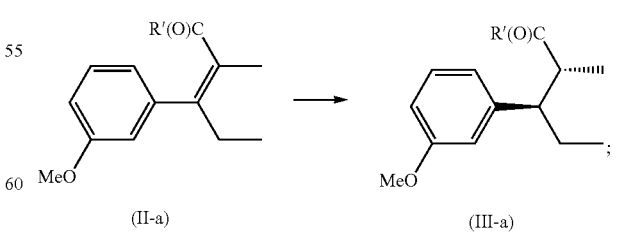

and optionally, when R' is other than NMe$_2$, converting the compound of formula (III-a) to the compound of formula (IV-a):

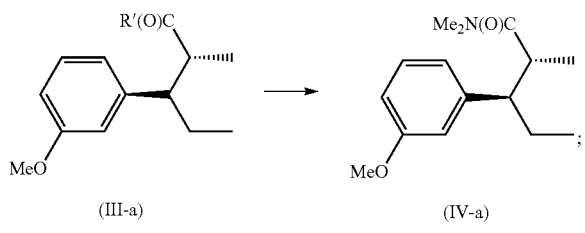

(III-a) → (IV-a)

or b2) and c2) optionally, when R' is other than NMe₂, converting the compound of formula (II-a) to a compound of formula (V-a); and

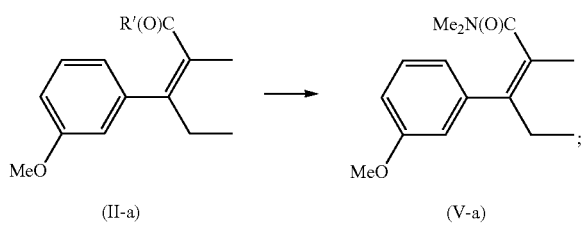

(II-a) → (V-a)

and hydrogenating the compound of formula (V-a) in the presence of a chiral catalyst to obtain the compound of formula (IV-a):

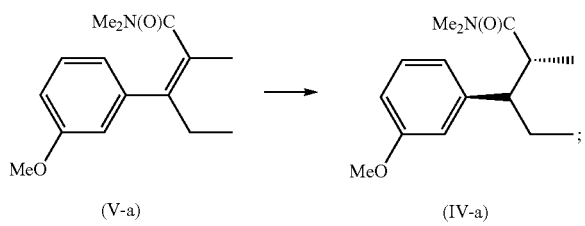

(V-a) → (IV-a)

d) reducing the resultant compound of formula (IV-a) obtained by step (c1) or (c2) to (1R,2R)-3-(3-methoxyphenyl)-N,N,2-trimethylpentan-1-amine of formula (VI-a):

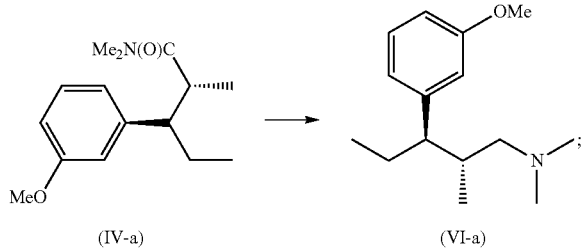

(IV-a) → (VI-a)

and e) converting (1R,2R)-3-(3-methoxyphenyl)-N,N,2-trimethylpentan-1-amine to 3-[(1R,2R)-3-(dimethylamino)-1-ethyl-2-methylpropyl]phenol (Tapentadol)

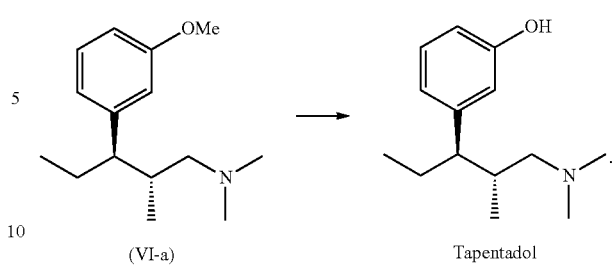

(VI-a) → Tapentadol

The process may further comprise the step of converting the compound of formula (A) or its precursor of formula (VI) to its pharmaceutically acceptable salt. For example, when the compound of formula (A) is Tapentadol, the process may comprise the step of converting Tapentadol or its precursor of formula (VI-a) to its pharmaceutically acceptable salt, preferably the hydrochloride salt.

The present invention further relates to certain intermediates produced in the above-described processes. According to a first aspect, the present invention provides a phosphonate compound represented by the structure of formula I-a:

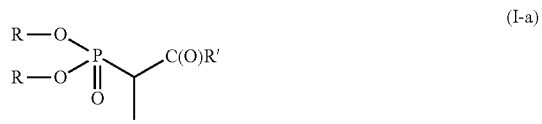

(I-a)

wherein each R is independently alkyl or aryl which is optionally substituted with an electron withdrawing group, preferably wherein R is 2,2,2-trifluoroethyl, phenyl or o-tolyl, and R' is $N(CH_3)_2$.

In one embodiment, the phosphonate compound represented by the structure of formula (I-a) is used for the preparation of compounds with a carbon-carbon double bond, such as but not limited to Tapentadol.

According to a second aspect, the present invention provides a compound represented by the structure of formula (II):

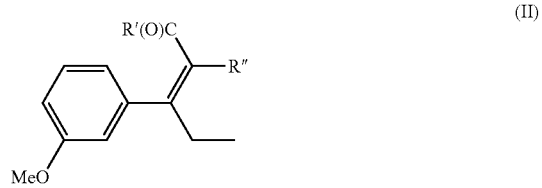

(II)

wherein R' is —NR¹R² wherein $R^1$ and $R^2$ are each alkyl, preferably wherein $R^1$ and $R^2$ are each methyl; and R" is alkyl, aryl, heteroalkyl, heteroaryl, alkylaryl or cycloalkyl, preferably wherein R" is methyl. Preferably, each of $R^1$, $R^2$ and R" is methyl.

In one embodiment this compound exists as Z-isomer. In another embodiment, this compound exists as a mixture of Z- and E-isomers. In one embodiment, R" in compound (II) is methyl, and the compound is represented by the structure of formula (II-a):

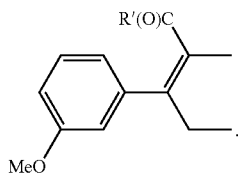

(II-a)

Each possibility represents a separate embodiment of the present invention.

According to a third aspect, the present invention provides a compound represented by the structure of formula (III), or a stereoisomer thereof. In some embodiments, this compound exists in optically active form, preferably as a threo-isomer. In some embodiments, this compound exists as a racemic mixture. Each possibility represents a separate embodiment of the present invention.

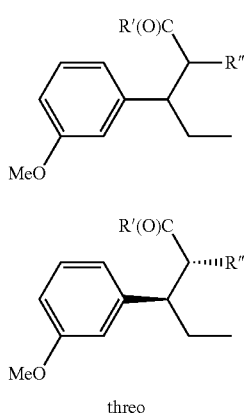

(III)

(III) threo wherein R' is (i) —$NR^1R^2$ wherein $R^1$ and $R^2$ are each alkyl, preferably wherein $R^1$ and $R^2$ are each methyl; (ii) —$OR^3$ wherein $R^3$ is alkyl, aryl or alkylaryl; or (iii) a functional group which can be converted to an amine group, preferably $NMe_2$ group; and R" is alkyl, aryl, heteroalkyl, heteroaryl, alkylaryl or cycloalkyl, preferably wherein R" is methyl.

According to a fourth aspect, the present invention provides an amide compound represented by the structure of formula (IV), or a stereoisomer thereof. In some embodiments, this compound exists in optically active form, preferably as a threo-isomer:

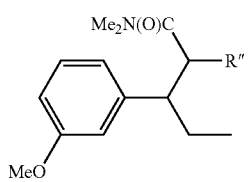

(IV)

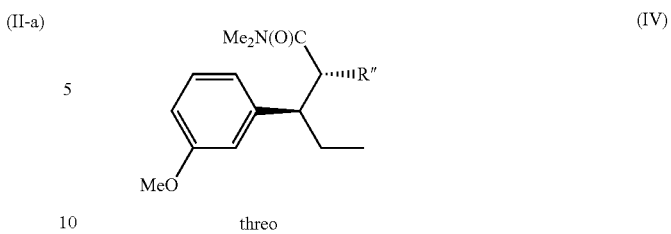

(IV) threo wherein R" is alkyl, aryl, heteroalkyl, heteroaryl, alkylaryl or cycloalkyl, preferably wherein R" is methyl.

In other embodiments, this compound exists as a racemic mixture.

In one embodiment, R" in compound (IV) is methyl, and the compound is represented by the structure of formula (IV-a), or a stereoisomer thereof, preferably the threo isomer.

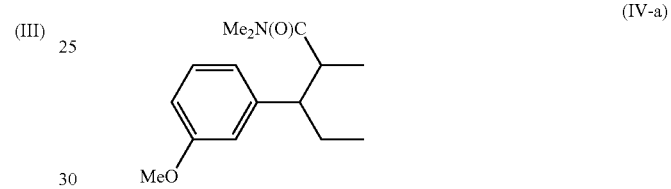

(IV-a)

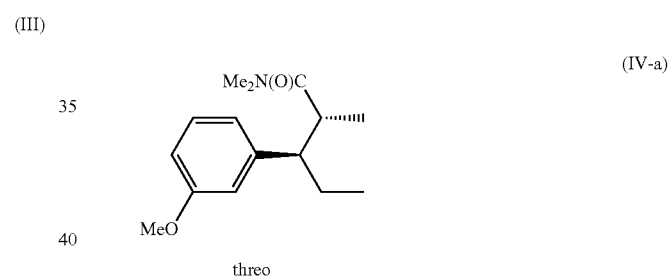

(IV-a) threo

According to a fifth aspect, the present invention provides an amide compound represented by the structure of formula (V):

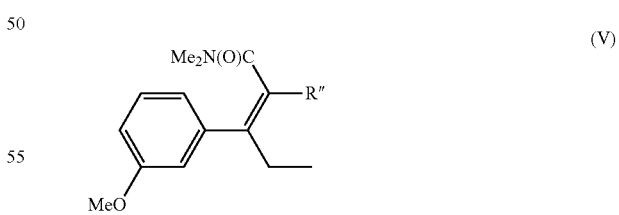

(V)

wherein R" is alkyl, aryl, heteroalkyl, heteroaryl, alkylaryl or cycloalkyl, preferably wherein R" is methyl.

one embodiment this compound exists as Z-isomer. In another embodiment, this compound exists as a mixture of Z- and E-isomers.

In one embodiment, R" in compound (V) is methyl, and the compound is represented by the structure of formula (V-a):

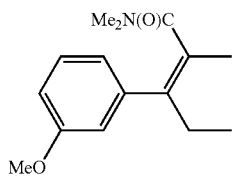

(V-a)

Chemical Definitions

An "alkyl" group refers to any saturated aliphatic hydrocarbon, including straight-chain, branched-chain and cyclic alkyl groups (cycloalkyl). In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. A "heteroalkyl" is an alkyl group containing one or more heteroatoms, such as S, O, N, etc.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Non-limiting examples of monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "aryl" group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. An "alkylaryl" group is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "electron-withdrawing group" as used herein refers to a substituent which attracts valence electrons from neighboring atoms, i.e., the substituent is electronegative with respect to neighboring atoms. Non-limiting examples of electron-withdrawing groups include nitro, acyl, formyl, sulfonyl, trifluoromethyl, cyano, halo, and the like. In some embodiments, the electron-withdrawing group is 2,2,2-trifluoroethyl.

The term "a functional group which can be converted to an amine group" as used herein includes, but is not limited to groups which comprise a leaving group, such as (i) halogen (F, Cl, Br, I), more preferably, Cl;

(ii) —$OR^a$ groups, wherein $R^a$ is $C_1$ to $C_6$ straight or branched alkyl, $C_6$ to $C_{10}$ aryl, or $C_7$ to $C_{12}$ alkylaryl. Preferably, $R^a$ is $C_1$ to $C_4$ straight or branched alkyl, phenyl or benzyl. More preferably, R is methyl or ethyl;

(ii) $N_3$;

(iii) Imidazolyl;

(iv) $^-OR^b$ wherein $R^b$ is derived from 1-hydroxy-7-azabenzotriazole, 1-hydroxybenzotriazole, N-hydroxymaleimide, N-hydroxy-5-norbornene-2,3-dicarboxylic acid imide, N-hydroxyphthalimide, N-hydroxysuccinimide, N-hydroxysulfosuccinimide sodium salt, 2-, 3-, or 4-nitrophenol, pentafluorophenol, 2,4,5-trichlorophenol, ethoxyacetylene, and the like;

(v) $^-OR^c$, wherein $R^c$ is acyl, dialkyl- or diarylphosphate or other derivatives of phosphorus containing acid, boron containing derivatives and the like; or (vi) $OR^d$, wherein $R^d$ is isourea, derived from carbodiimides, such as dicyclohexyl carbodiimide (DCC), diisopropyl carbodiimide (DIC) 1-ethyl-3-(3'-dimethylamino) carbodiimide HCl salt (EDC or WSC) and the like;

(vii) —$SR^e$, wherein $R^e$ is derived from 2-mercaptopyridine, 2-thiazoline-2-thiol and the like; and (viii) derivatives of cyanuric chloride or fluoride, such as 4-(4,6-dimethoxy-(1,3,5)-triazin-2-yl)-4-methyl-morpholinium chloride (DMTMM); isoxazolium salts such as N-ethyl-5-phenylisoxazolium-3'-sulfonate, N-ethylbenzisoxazolium tetrafluoroborate; Mukaiyama's reagent-2-chloro-1-methylpyridinium iodide and the like, such as 2-bromo-3-ethyl-4-methylthiazolium tetrafluoro-borate (BEMT).

Each possibility represents a separate embodiment of the present invention.

The term "isomer", as used herein, includes all possible geometric isomers as well as stereoisomers and conformational forms, made up of the same atoms bonded by the same sequence of bonds but having different three-dimensional structures which are not interchangeable. Stereoisomers include diastereomers, enantiomers and/or conformers of the basic molecular structure of said compound. More in particular, stereogenic centers (also referred to as chiral centers) can be designated as R or S or R,S or d,D, l,L or d,l, D,L. In addition, some compounds of the invention contain one or more double bonds. The present invention encompasses all structural and geometrical isomers including cis, trans, E and Z isomers, independently at each occurrence. Any combinations of the above features are also contemplated.

The term "diastereomer" applies to molecules with identical chemical constitution and containing more than one stereocenter, which differ in configuration at one or more of these stereocenters. Diastereomers may have a syn- or anti- configuration.

The term "enantiomer" applies to molecules with identical chemical constitution and containing one or more stereocenters, where each stereocenter of one enantiomer differs from the corresponding stereocenter of the other enantiomer.

All stereoisomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), diastereomerically enriched mixtures (i.e., mixtures enriches for one diastereomer), pure enantiomers or diastereomers, or any mixtures thereof.

Pure stereoisomeric forms refer to isomers substantially free of other enantiomeric or diastereomeric forms of the same basic molecular structure of said compounds or starting material. Suitably, the terms "stereoisomerically pure or enriched" compounds relate to compounds having a stereoisomeric excess of at least about 50% (i.e. minimum of about 75% of one isomer and maximum of about 25% of the other possible isomers) up to a stereoisomeric excess of about 100% (i.e. about 100% of one isomer and none of the other), preferably, compounds having a stereoisomeric excess of about 75% up to about 100%, more preferably, compounds having a stereoisomeric excess of about 90% up to about 100%, even more preferred compounds having a stereoisomeric excess of about 94% up to about 100% and most preferred, having a stereoisomeric excess of about 97% up to about 100%. The terms "enantiomerically enriched or pure" and "diastereomerically enriched or pure" are similarly defined, but refer to the enantiomeric or diastereomeric excess, respectively of the mixture in question.

The process of the invention, as applied for the preparation of Tapentadol, is exemplified in the non-limiting embodiments set forth in Schemes 11 and 12. It is apparent that the process of the present invention can be further embodied and used to prepare other compounds of formula (A) and related compounds, as described herein.

Scheme 11

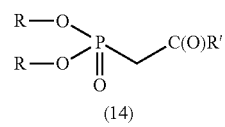

(14)

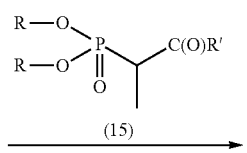

(15)

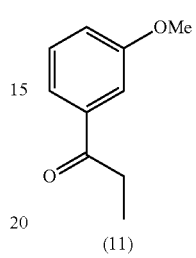

(11)

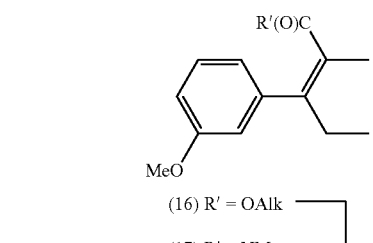

(16) R' = OAlk
(17) R' = NMe$_2$

Scheme 12

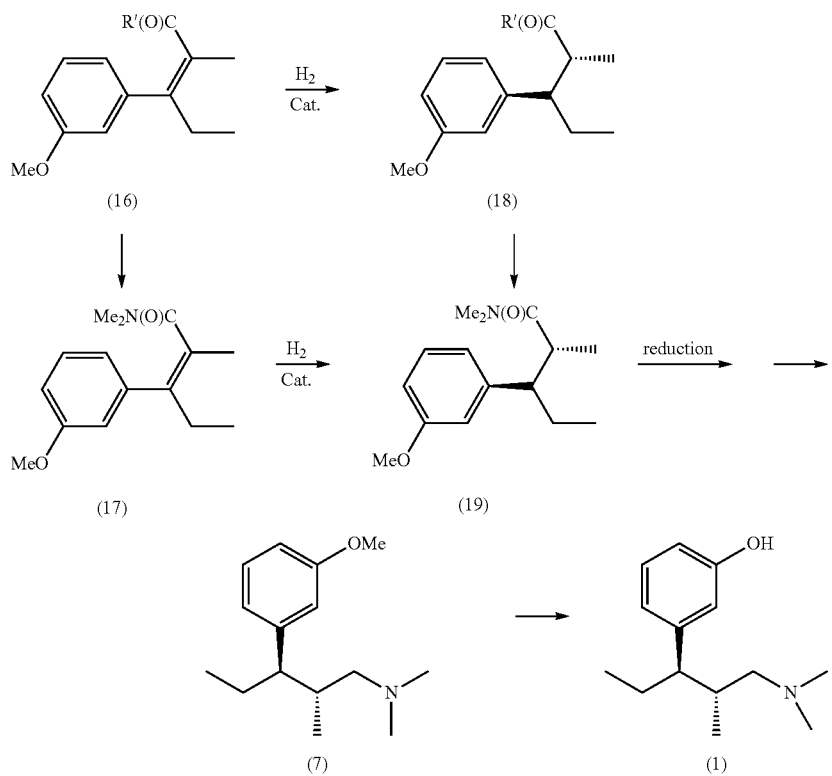

The process includes the following steps:

a). Preparation of a Tapentadol intermediate of formula (16), via a Horner-Wadsworth-Emmons (HWE) reaction between 1-(3-methoxy-phenyl)-propan-1-one (11) and phosphonate (15), wherein R is alkyl or aryl, preferably containing electron withdrawing group, such as 2,2,2-trifluoroethyl; phenyl or o-tolyl; and R' is (i) —$NR^1R^2$ wherein $R^1$ and $R^2$ are each alkyl; (ii) —$OR^3$ wherein $R^3$ is alkyl, aryl or alkylaryl; or (iii) a functional group which can be converted to an amine group, preferably $NMe_2$ group.

In one embodiment, R' is $OR^3$ wherein $R^3$ is a group which can be removed by action of amine, for example, $R^3$ is a straight or branched alkyl, aryl, and alkylaryl. In another embodiment, $R^3$ is $C_1$ to $C_4$ straight or branched alkyl, phenyl or benzyl. In one currently preferred embodiment, $R^3$ is methyl or ethyl. A compound of formula (16), wherein R' is O-Alk (i.e., O-alkyl), is preferably used in this step. Another currently preferred embodiment is when R' is $NR^1R^2$ wherein each of $R^1$ and $R^2$ are methyl ($CH_3$, Me), i.e., R'=$N(CH_3)_2$, i.e., $NMe_2$).

If R' is other than $NMe_2$, the ester group of (16) is converted to the dimethylamide group of derivative (17). If R' is $NMe_2$, no such step is performed, and compound (17) is obtained directly from reaction of (11) and (15). Each possibility represents a separate embodiment of the present invention.

b) and c). Olefin (16) or (17) are then hydrogenated using organometallic catalyst. Preferably, the reduction is a stereoselective reaction, which results in optically active (18) or (19). However, non-stereoselective reduction which results in a racemic product is also contemplated. Alternatively, olefin (16) can be hydrogenated to ester (18) and then transformed to amide (19), or olefin (16) can be converted to amide (17) which is then hydrogenated to amide (19). Thus, the process may comprise hydrogenation followed by amidation (steps (b1) and (c1)); or amidation followed by hydrogenation (steps (b2) and (c2)), or simply hydrogenation when R' is $NMe_2$ (in which case optional steps (b2) and (e1) are not performed). Each possibility represents a separate embodiment of the present invention.

d). The next step involves reduction of amide group of (19) to amine (7):

e). Finally, the process includes the step of deprotection of phenol group in (7) to the desired compound (1).

These steps individually, and in any combination, as well as the compounds that result from such steps are considered to be part of the invention as well. This process is described in more detail in the discussion and examples below. It is apparent to a person of skill in the art that the description is non-limiting and that various modifications may be made and alternative embodiments practiced, as is apparent to a person of skill in the art.

Step (a):

Compound (11), which is used here as a raw material is an available reagent and can be produced by well-known methods as described, for example, in WO2007/044796A2, the contents of which are incorporated by reference herein.

Phosphonate (15) can be prepared by a Michaelis-Arbusov reaction [Bhattacharyai, A. K.; Thyagarajan, G. *Chem. Rev.* 1981, 81, 415-430]; Michaelis-Becker Reaction [Worms, K. H.; Schmidt-Dunker, M. In *Organic Phosphorus Compounds*; Kosolapoff, G. M. and Maier, L. Ed.; Wiley: New York, 1976, Vol. 7, pp. 27-28; Muller, E. (ed.) *Methoden der Organishen Chemie* (Houben-Weyl); George Theime Verlag: Stuttgart, 1964, Vol 12/1, p. 446]; by acylation of alkylphosphonate anions [Organic Syntheses, Coll. Vol. 9, p. 88 (1998); Vol. 73, p. 152 (1996)] or by phosphonate ester interchange [Still, W. C.; Gennari, C. *Tetrahedron Lett.* 1983, 24, 4405-4408; Bodnarchuk, N. D.; Malovik, V. V.; Derkach, G. I. Zh. Obshch. Khim. 1970, 40, 1210]. Some examples of phosphonate (15) preparations are presented in the experimental section. The contents of the aforementioned references are incorporated by reference herein in their entirety.

Compounds (16) and (17) (or more generally compounds (II), (II-a), (V) or (V-a)) represent tetrasubstituted olefins, bearing four different carbon-linked groups. The efficient regio- and stereoselective synthesis of such compounds presents a particular challenge in organic synthesis. Currently, the most frequently used routes to tetrasubstituted olefins employ different types of alkynyl carbometallation strategies, although another common technique is the transformation of existing olefins [A. B. Flynn and W. W. Ogilvie. Stereocontrolled Synthesis of Tetrasubstituted Olefins. Chem. Rev. 2007, 107, 4698-4745]. Strategies such as olefin metathesis, radical sequences, and ynolate chemistry are emerging as viable techniques for the formation of tetrasubstituted olefins [Mitsuru Shindo, Seiji Mori. Torquoselective Olefination of Carbonyl Compounds with Ynolates: Highly Efficient Stereoselective Synthesis of Tetrasubstituted Alkenes. [SYNLET, 2008, No. 15, pp 2231-2243]. The contents of the aforementioned references are incorporated by reference herein in their entirety. Any of these methods can be used to prepare the alkene compounds in the process of the present invention.

Other classical double bond-forming methods are the Wittig and Horner-Wadsworth-Emmons (HWE) reactions, of which the HWE is currently preferred for the process described in the present application. There are several promising approaches which are based on convenient preparation of tetrasubstituted alkenes with excellent selectivity, based on reaction of methyl bis(2,2,2-trifluoroethyl)-phosphonoacetate or ethyl 2-fluoro-2-diethylphosphonoacetate with aryl alkyl ketones by using metal trifluoromethanesulfonates and tertiary amines [Sano S., Yokoyama K., Fukushima M., Yagi T., Nagao Y., *Chem. Commun.*, 559-560 (1997); Sano S., Ando T., Yokoyama K., Nagao Y., *Synlett*, 777-779 (1998); Sano S., Yokoyama K., Teranishi R., Shiro M., Nagao Y., *Tetrahedron Lett.*, 43, 281-284 (2002); Sano S., Yokoyama K., Shiro M., Nagao Y., *Chem. Pharm. Bull.*, 50, 706-709 (2002)]. The contents of the aforementioned references are incorporated by reference herein in their entirety.

These methods, and especially the HWE reaction, can be adapted to the process of the present invention. However, it is apparent to a person of skill in the art that other methods can be used to generate the compounds of formulae (16) and (17), or more generally the compounds of formulae (II), (II-a), (V) and (V-a).

In one embodiment, the present invention is directed to a process for preparing a Tapentadol intermediate of formula (16), or more generally compounds of formula (II) or (II-a), or their amide derivatives (V) and (V-a), via a reaction of 1-(3-methoxy-phenyl)-propan-1-one (11) and phosphononate (15) in the presence of additives. Non-limiting examples of additives are metal trifluoroacetates or trifluoromethanesulfonates (triflates), such as lanthanide triflates, for example, $La(OTf)_3$, $Y(OTf)_3$, $Yb(OTf)_3$, $Sc(OTf)_3$, $Hf(OTf)_4$, $Ga(OTf)_3$, preferably, cerium triflate, or $Al(OTO_3$, $Ti(OTf)_4$, $Zn(OTf)_2$, $Fe(OTf)_3$, preferably, $Sn(OSO_2CF_3)_2$ along or in the combination with amine, preferably, tertiary amine, such as triethylamine, diisopropylethylamine, N-methylmorpholine, pyridine, lutidine and picoline, preferably, N-ethylpiperidine.

Other additives are inorganic and organic bases, which include, but are not limited to, alkali metal and alkaline earth hydrides, and alcoholates, for example potassium hydride, sodium hydride, calcium hydride, sodium methoxide, sodium ethoxide, potassium tert-butoxide, and the like, alkali metal amides, such as potassium bis(trimethylsilyl)amide; tertiary amines such as DNU, DBN, diisopropylethylamine along or in the presence of salts, such as alkali or alkaline earth metal halogenides, for example, lithium chloride or bromide. Base to which current preference is given is sodium hydride.

Preferably, the reaction in the presence of $Sn(OSO_2CF_3)_2$ and amine is carried out at a temperature between about $-10°$ C. and about $80°$ C., for example at reflux temperature. The reaction is conducted in any suitable solvent, which may for example be selected from the group consisting of $C_6$ to $C_{14}$ aromatic hydrocarbons, $C_2$ to $C_7$ esters, $C_4$ to $C_7$ ethers, $C_1$ to $C_5$ carboxylic acid amides such as DMF, halogenated hydrocarbons, or suitable mixtures of these solvents in any ratios. Currently Preferred solvents are halogenated hydrocarbons, such as methylene chloride (dichloromethane), ethylene chloride (dichloroethane), chlorobenzene, and dichlorobenzene.

Preferably, the reaction in the presence of sodium hydride or other base additive is carried out at a temperature between about $-10°$ C. and about $80°$ C., for example at reflux temperature. The reaction is conducted in any suitable solvent, which may for example be selected from the group consisting of $C_6$ to $C_{14}$ aromatic hydrocarbons, $C_2$ to $C_7$ esters, $C_4$ to $C_7$ ethers, $C_1$ to $C_5$ carboxylic acid amides such as DMF, halogenated hydrocarbons, or suitable mixtures of these solvents. Preferred solvents are ethers, such as THF or carboxylic acid amides such as DMF, or mixtures of these solvents in any ratios.

Phosphonate (15) (or more generally compounds of formula (I) or (I-a)) which bears electron withdrawing group(s) tends to yield tetrasubstituted alkenes (16) and (17) (or more generally compounds (II), (II-a), (V) or (V-a)) as predominately the Z-isomer.

Phosphonate (15) (or more generally compounds of formula (I) or (I-a)) wherein R=Alk, Aralkyl tends to yield tetrasubstituted alkenes (16) and (17) (or more generally compounds (II), (II-a), (V) or (V-a)) as a mixture of E- and Z-isomers.

The process of the invention for formation of the carbon-carbon double bond 25 contemplates the generation of the Z-isomer predominantly, mixtures of the E- and Z-isomers, or formation of the E-isomer predominantly. In the case where mixtures of the E- and Z-isomers are formed, they can contain the two isomers in any ratio.

Compounds (16) and (17) (or more generally compounds (II), (II-a), (V) or (V-a)) are pure enough to be used in the next step, but if necessary, they can be purified by any suitable technique, for example, by crystallization or column chromatography.

In case the relatively expensive trifluoroethanol derivatives of phosphoric acid are formed as by-product in HWE reaction, they can be recycled in the form of trifluoroethanol and then reused for the preparation of phosphononate (15) or similar phosphonate compounds of formula (I) or (I-a).

Optionally, ester (16) can be transformed to dimethylamide derivative (17) directly by reaction with dimethylamine similar to the procedure described in [Organic Syntheses, Coll. Vol. 7, p. 41 (1990); Vol. 61, p. 24 (1983)], the contents of which are incorporated by reference herein or, alternatively, indirectly by hydrolysis of ester (16) to corresponding acid (20) followed by amidation with dimethylamine:

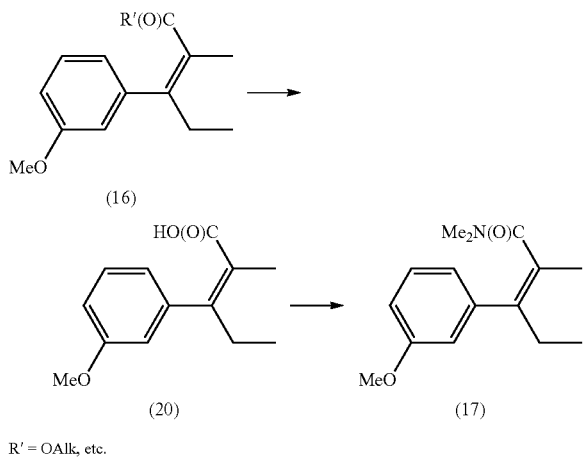

R' = OAlk, etc.

Hydrolysis of ester (16) to corresponding acid (20) (i.e., a saponification reaction) may be carried out in the presence of a base and an organic solvent. Suitable bases include, but are not limited to, alkali metal and alkaline earth carbonates and hydroxides, for example potassium bicarbonate, sodium bicarbonate, potassium carbonate, sodium carbonate, sodium hydroxide, potassium hydroxide, calcium hydroxide, and the like; primary, secondary, and tertiary amines such as piperidine, triethylamine, diisopropylethylamine, N-methylmorpholine, pyridine, lutidine and the like; ammonia and basic resins, and the like. Bases to which current preference is given are hydroxides, such as NaOH or KOH; especially preferred is NaOH. A suitable amount of base for saponification is, for example, at least about one equivalent for each ester group, preferably from about 1 to about 5 equivalents; more preferably from about 1 to about 3 equivalents. Suitable solvents include, but are not limited to alcohols, ethers, DMF, NMP, DMSO, water or suitable mixtures of these solvents. Each possibility represents a separate embodiment of the present invention. Some examples of preferred solvents are THF, or a THF-water mixture.

The saponification reaction is preferably carried out in a temperature range of from about $20°$ C. to about $100°$ C., especially from about $50°$ C. to about $75°$ C. The reaction time for saponification is generally from about 15 minutes to about 48 hours, preferably from about 30 minutes to about 18 hours, more preferably from about 1 to about hours. The said saponification can be carried out at normal, elevated or reduced pressure, preferably at normal pressure.

The base can be used as a solution in a suitable solvent, a preferred basic solution is a solution of inorganic hydroxide in water, such as a solution of sodium hydroxide in water.

Following saponification, the product is transferred without purification to an amidation step, which is typically carried out in the presence of activation reagents. Alternatively, hydrolysis of ester (16) can be carried out by an enzyme, for example, by porcine liver esterase (PLE, Sigma; E-2884).

The present invention further comprises a process for preparing an intermediate of formula (17), which comprises converting the —COOH group of compound (20) to an activated acid derivative (20A) followed by aminolysis of the activated acid derivative (20A) by dimethylamine or its salts or derivatives.

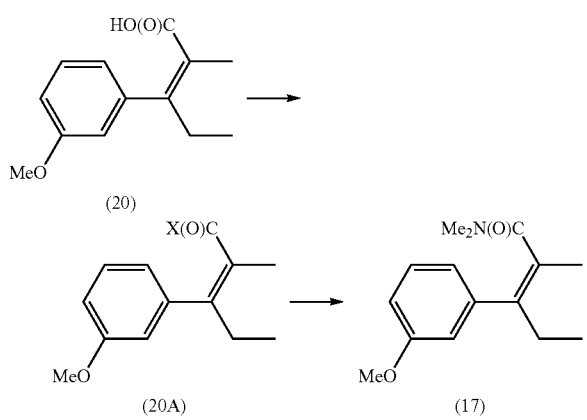

Suitable activated acid derivatives may be an acid chloride (X=Cl). Acid chloride formation can be performed by using thionyl chloride, oxalyl chloride, phosgene, POCl₃, PCl₃, PCl₅, and the like, preferably thionyl chloride. The acid chloride is treated with dimethylamine or a dimethylamine-generating reagent to produce the compound of formula (17). The reaction is preferably conducted in the presence of an organic solvent such as, but not limited to, halogenated hydrocarbons, aromatic hydrocarbons, esters, ethers, nitriles, ketones, amides and mixtures thereof; preferably dichloromethane, toluene, or diisopropyl ether.

Suitable activated acid derivatives may also be a mixed anhydride of acid (20), which may be prepared by any of the methods known in the art, for example by treatment with methyl-, ethyl or isopropyl chloroformate, pivaloyl chloride, or a Boc anhydride, preferably, Boc anhydride. Preparation of amide (17) may be carried out by introducing a solution of an activated carbonate such as Boc anhydride into a solution of compound (20) in an organic solvent in the presence of a base, so as to obtain a mixed anhydride, followed by contacting the mixed anhydride with dimethylamine or dimethylamine generating reagent. This reaction is also preferably conducted in the presence of an organic solvent such as, but not limited to halogenated hydrocarbons, aromatic hydrocarbons, esters, ethers, cyclic ethers, and mixture thereof; preferably ethyl acetate or THF; most preferably ethyl acetate. The organic base may be selected from triethylamine, diisopropylethylamine, N-methylmorpholine, pyridine, lutidine, and picoline, most preferably pyridine.

The same or similar conditions can be used to transform the more general compounds (II) or (II-a) to amides (V) or (V-a), via saponification to the corresponding carboxylic acid, and amidation.

Steps (b) and (c):

The next steps in the process of the invention relate to the preparation of a tapentadol intermediate of formula (18), comprising the reduction of a compound of formula (16) with a reducing agent, preferably hydrogen in the presence of suitable solid catalysts. Alternatively, the amide intermediate of formula (17) is reduced to a compound of formula (19). In yet another embodiment, intermediate (16) is reduced to compound (18), which is further converted to compound (19) via an amidation reaction. In yet another embodiment, intermediate (16) is converted to amide (17) which is reduced to a compound of formula (19). More generally, the process can be applied to the preparation of intermediates of formula (III) by reduction of formula (II) and, if R' is other than NMe₂, conversion of compounds (III) to an amide of formula (IV). Alternatively, compound (II) can first be amidated to a compound of formula (V), which is reduced to a compound of formula (IV). Each possibility represents a separate embodiment of the present invention.

Known solid catalysts used for hydrogenation can be used in the present invention. These include, but are not limited to, catalysts in which at least one member is selected from a group consisting of copper, zinc, nickel, ruthenium, palladium, platinum, rhodium, and oxides thereof. In such catalysts, at least one additional metal is used as a promoter and may be selected from a group consisting of chromium, molybdenum, tungsten, magnesium, barium, aluminum, calcium, zirconium, manganese, nickel, silicon, and their oxides.

The catalysts are typically used together with solid or liquid supports. Examples of supports used for such solid catalysts include silica, alumina, silica-alumina, titania, diatomaceous earth, kaolin, activated carbon, carbon, graphite, zeolite, montmorillonite and the like; clays; alkaline earth metal silicates, etc. These catalysts may be used as such, but are preferably subjected to a suitable activation treatment, such as reduction treatment, prior to use. Such activation treatment can be carried out by conventional methods known to a person of skill in the art.

Examples of nickel-based catalysts include, but are not limited to, Raney nickel, nickel-diatomaceous earth, nickel-chromium oxide, etc, preferably, Raney nickel. Noble-metal-based solid catalysts containing, for example, ruthenium, palladium, platinum, rhodium or oxides thereof include solid catalysts in which such metal or oxide thereof is supported by a support, such as silica, alumina, silica-alumina, titania, activated carbon, carbon, graphite or the like, preferably, Pd/C.

Suitable solvents for this reaction include, but are not limited to alcohols, especially lower alcohols such as methanol, ethanol, propanol or butanol, or ethylenglycol, diethylenglycol, ethylenglycolmonomethyl- or monoethylether, diethylenglycolmonomethyl- or monoethylether or ketones such as acetone or methylisobutylketone. The solvent may also be a mixture of solvents or a mixture of a solvent or solvents with water, for example a mixture of methanol with water, in any ratios. Preferred solvents are ethanol and isopropanol.

The hydrogenation is carried out for example with a hydrogen pressure of up to about 200 bar, preferably with a hydrogen pressure of about 1 to about 200 bar and most preferred with a hydrogen pressure of about 5 to about 40 bar. The reaction is carried out, for example, at a temperature between about 0° and about 80° C., especially between about 25° to about 30° C. 25

Optionally, olefin (16) can be hydrogenated to ester (18) and then transformed to amide (19) by the above described methods for amide bond formation.

In another embodiment, the present invention comprises a process for preparing of compound (18) by asymmetric hydrogenation of tetrasubstituted alkene (16), and compound (19) by asymmetric hydrogenation of tetrasubstituted alkene (17), wherein compounds (16) and (17) are a mixture of E- and Z-isomers. More generally, the present invention comprises a process for preparing of compound (III) by asymmetric hydrogenation of tetrasubstituted alkene (II), and compound (IV) by asymmetric hydrogenation of tetrasubstituted alkene (V), wherein compounds (II) and (V) are a mixture of E- and Z-isomers. In another embodiment, the present invention comprises a process for preparing of compound (III-a) by asymmetric hydrogenation of tetrasubstituted alkene (II-a), and compound (IV-a) by asymmetric hydrogenation of tetrasubstituted alkene (V-a), wherein compounds (II-a) and (V-a) are a mixture of E- and Z-isomers.

Known catalysts used for asymmetric hydrogenation of tetrasubstituted carbon-carbon double bonds can be used as catalysts in the present invention. Among such catalysts complexes of transition metals, such as rhodium, ruthenium, iridium, platinum, titanium, zirconium and palladium are most effective. Optionally, the catalyst can be associated with or attached to a chiral ligand, for example a chiral phosphorus ligand.

Examples of ruthenium-based catalysts include, but not limited to $Ru_2Cl_4[(R)\text{-BINAP}]_2N(C_2H_5)_3$, {RuCl(Benzene)[(R)-BINAP]}Cl, {RuCl(p-Cymene)[(R)-BINAP]}Cl, {RuBr(p-Cymene)[(R)-BINAP]}Br. Preferably, Ru catalysts are prepared in situ by protonation of a mixture of Ru(COD)-(methallyl)$_2$ and a chiral bisphosphorus ligand with two equivalents of $HBF_4$. A known chiral bisphosphorus ligand used for asymmetric hydrogenation catalysis [*Chem. Rev.* 2003, 103, 3029-3069, the contents of which are incorporated by reference herein] can be used as a ligand in the process of present invention, preferably, (S,S)-DIOP, (R,R)-Me-DuPhos, (S,S,R,R)-TangPhos, (S)-Cn-TunaPhos, where n=1-6, most preferably (S)-BINAP, (S)-MeO-BIPHEP or C3-TunaPhos:

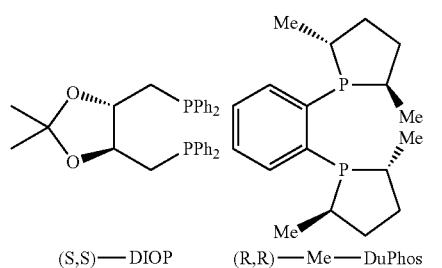

(S,S)—DIOP     (R,R)—Me—DuPhos

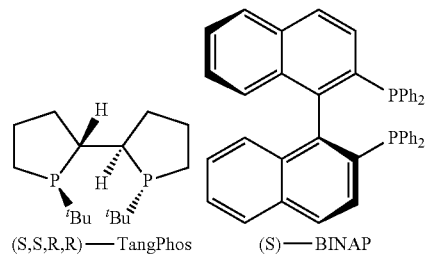

(S,S,R,R)—TangPhos     (S)—BINAP

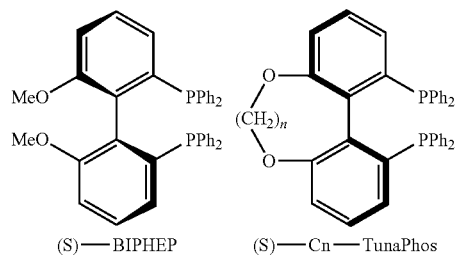

(S)—BIPHEP     (S)—Cn—TunaPhos n = 1-6

Examples of rhodium-based catalysts suitable for use in the process of the present invention include, but not limited to rhodium complexes [Rh(diene)Cl]$_2$, where diene is 1,5-hexadiene, 1,5-cyclooctadiene, norbornadiene, coordinated with chiral phosphine ligands, preferably, with (aminoalkyl)-ferrocenylphosphine ligands, for example, (R)-N-methyl-N-[2-(dialkylamino)ethyl]-1-[S)-1',2-bis(diphenylphosphino) ferrocenyl]ethylamines:

(21)

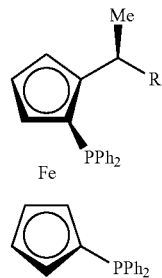

wherein R=(a) —N(CH$_2$)$_5$; (b) NEt$_2$; (c) NBu$_2$; (d) —N(CH$_2$)$_4$—

The complexes were prepared by mixing of [Rh(nbd)$_2$]BF$_4$, (nbd=norbornadiene) [Organic Syntheses, Vol. 82, p. 22 (2005)] with available ferrocenylphosphines [WO 2005/068478]. The contents of these references are incorporated by reference herein.

Additional example of rhodium complexes is [Rh(1,5-cyclooctadiene) (BPPM)]$^+$ClO$_4^-$ where chiral phosphine ligands can be pyrrolidine phosphines of formula [Tetrahedron Letters, 1978, No. 29, pp. 2583-2584, the contents of which are incorporated by reference herein]:

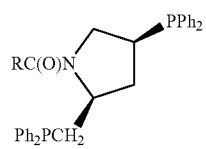

wherein

| | |
|---|---|
| RCO—=(CH$_3$)$_3$COCO— | (BPPM) |
| RCO—=HCO— | (FPPM) |
| RCO—=CH$_3$CO— | (APPM) |
| RCO—=C$_6$H$_5$CO— | (BZPPM) |
| RCO—=(CH$_3$)$_3$CCO— | (PPPM) |

Examples of iridium-based catalysts suitable for use in the process of the present invention include, but not limited to Ir(Py)(PCy$_3$)(COD)]PF$_6$ (Crabtree catalyst), Ir(COD)(BINAP)]BARF, iridium complexes with phosphino-oxazoline (PHOX) ligands of general formula:

(22)

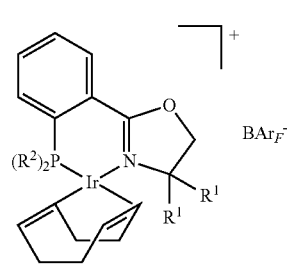

R$^1$=Me, R$^2$=Ph

R$^1$=H, R$^2$=Ph

R¹=Me, R²=Cy

R¹=H, R²=Cy

BAr$_F$=tetrakis[3,5-bis(trifluoromethyl)phenyl]borate

The above mentioned catalysts for asymmetric hydrogenation can be used as homogeneous catalysts or they can be grafted to insoluble support forms to form heterogeneous catalysts.

The hydrogenation is carried out for example with a hydrogen pressure of up to about 200 bar, preferably with a hydrogen pressure of about 1 to about 200 bar and most preferred with a hydrogen pressure of about 50 to about 100 bar. The reaction is carried out, for example, at a temperature between about 0° and about 80° C., especially between about 25° to about 30° C.

Step (d):

In the next step, the tapentadol intermediate (7) is prepared via reduction of compound (19) with a reducing agent. More generally, this step can involve reduction of the intermediate (IV) to generate amine (VI), or reduction of (IV-a) to generate amine (VI-a).

The reducing agent can be, for example borane and its complexes with dimethylsulfide, pyridine, triethylamine and the like; lithium and sodium borohydride in the presence of a Lewis acid, such as boron trifluoride diethyl ether complex, aluminum-, titanium- or cobalt-chlorides and the like, or in the presence of trimethylchlorosilane or phosphorus oxychloride; or an aluminum hydride such as AlH$_3$ and its complexes with amines, LiAlH$_4$, sodium bis(2-methoxyethoxy)aluminium hydride (Red-Al) or diisobutylaluminum hydride. Preferably the reducing agent is sodium borohydride in the presence of boron trifluoride diethyl ether complex.

Step (e):

Finally, tapentadol base is prepared by deprotecting the OH-group of the aromatic ring of compound (7). More generally, a compound of formula (A) is prepared by deprotecting the OH-group of the aromatic ring of compound (VI).

The deprotection can be carried out by using reagents such as, but not limited to BBr$_3$, HBr in acetic acid, pyridine-HBr, quarternary ammonium salt, 2-(diethylamino)-ethanethiol. HCl, trifluoroacetic acid, anisole and AlCl$_3$, preferably by concentrated hydrobromic acid. The desired compound is extracted from the reaction mixture by a suitable solvent. Suitable solvents include halogenated hydrocarbons, a C$_6$ to C$_{14}$ aromatic hydrocarbon, a C$_1$ to C$_7$ aliphatic hydrocarbon, a C$_2$ to C$_7$ ester, and a C$_2$ to C$_7$ ether or a suitable mixture of these solvents in any ratio. A preferred solvent is dichloromethane or dichloroethane.

Tapentadol hydrochloride can be separated from the dichloromethane or dichloroethane solution as a hydrochloride salt by addition of hydrogen chloride or hydrogen chloride generating mixtures. Other suitable pharmaceutically acceptable salts can be prepared in a manner known to a person of skill in the art. Thus, in some embodiments, the present invention further includes the step of converting the compound of formula (I), or more generally the compounds of formula (A) to their pharmaceutically acceptable salts. The term "Pharmaceutically acceptable salts", as used herein, refers to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. For example, non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

In the case of Tapentadol, a preferred salt is the hydrochloride salt. However, other salts with inorganic and organic acids are also contemplated.

EXAMPLES

Specific compounds which are representative of this invention were prepared as per the following examples and reactions sequences. No attempt has been made to optimize the yields obtained in any of the reactions. One skilled in the art would know how to increase such yields through routine variations in reaction times, temperatures, solvents and/or reagents. Unless otherwise noted, the materials used in the examples were obtained from readily available commercial suppliers or synthesized by standard methods known to one skilled in the art of chemical synthesis. The work-up treatment in each step can be applied by a typical method, wherein isolation and purification is performed as necessary by selecting or combining conventional methods, such as crystallization, recrystallization, distillation, partitioning, silica gel chromatography, preparative HPLC and the like.

Starting materials were prepared according to following procedures:

tris(2,2,2-trifluoroethyl)phosphite; bis(2,2,2-trifluoroethyl) phosphate; bis(2,2,2-trifluoroethyl)phosphoro chloridate [J. Fluorine Chem., 113, p. 65 (2002)]

bis-(2,2,2-trifluoroethyl)phosphonoacetic acid [ARKIVOC 2003 (viii) 93-101]

Ethylphosphonic acid bis-(2,2,2-trifluoroethyl)ester [Organic Syntheses, Vol. 82, p. 147 (2005)]

methyl 2-(bis(2,2,2-trifluoroethoxy)phosphoryl)propanoate [Chem. Pharm. Bull. 50(9) 1300-1302 (2002)]

2-chloro-N,N-dimethylacetamide [Huaxue Shiji, 28(6), 371-372, 2000; Faming Zhuanli Shenqing Gongkai Shuomingshu, 1721392, 18 Jan. 2006; JP 59098075 (1984); JP 04011542 (1992)]

2-bromo-N,N-dimethylacetamide [J. Org. Chem. 1982, 47, 1284-1291]

The contents of the aforementioned publications are incorporated by reference herein.

Example 1

Preparation of bis(2,2,2-trifluoroethyl) 2-(dimethylamino)-2-oxoethylphosphonate (14)

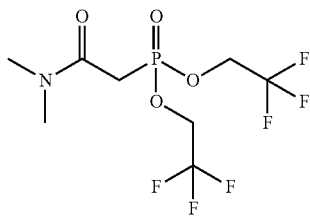 [SMILES: CN(C)C(=O)CP(=O)(OCC(F)(F)F)OCC(F)(F)F]

(i) By Michaelis-Becker Reaction a). To a solution of imidazole (2.084 g, 30 mmol) in CH$_2$Cl$_2$ (20 mL) was added PCl$_3$ (0.88 mL, 10 mmol) and then 2,2,2-trifluoroethanol (20 mmol) at 0° C. After stirring for 30 min, water (0.18 mL, 10 mmol) was added. The salt was removed by filtration, and the filtrate was treated with 2-bromo-N,N-dimethylacetamide (8 mmol) and triethylamine (1.69 mL, 12 mmol) at 0° C. for 10 min. The mixture was stirred for 5 h at 25 room temperature. The reaction was quenched with water (20 mL). Extraction and column chromatography (silica gel 35 g/hexane-AcOEt (8:1 to 5:1)) provided bis(2,2,2-trifluoroethyl) 2-(dimethylamino)-2-oxoethylphosphonate (48% from 2-bromo-N,N-dimethylacetamide) as a colorless oil.

$^1$H NMR (400 MHz, CDCl$_3$) δ: 3.25 (d, J=21.6 Hz, 2H), 3.47 (s, 6H), 4.43 (dq, J=8.3, 8.2 Hz, 4H); $^{13}$C NMR (100 MHz, CDCl$_3$) δ: 37.1 (s, NMe$_2$), 40.0 (d, J=145 Hz, P(O)CH$_2$C(O)), 62.3 (2, dq, J=39.1, 5.6 Hz, CF$_3$CH$_2$), 122.4 (2, dq, J=277.4, 8.4 Hz, CF$_3$), 169.4 (d, J=4.4 Hz, C=O); $^{31}$P NMR (CDCl$_3$) δ: 24.67.

b). Bis(2,2,2 trifluoroethyl)phosphite (5.0 mmol, 0.79 mL) was added to a solution of sodium hydride (0.420 g, 0.018 mol) and HMPA (8.6 mmol, 1.5 mL) at 10° C. in THF (20 mL). Immediately after addition, 2-bromo-N,N-dimethylacetamide (3.9 mmol) was added dropwise. The reaction temperature was maintained at 10° C. for 4.5 hours. The reaction was then quenched with saturated aqueous ammonium chloride (2 mL) and standard aqueous work-up was performed. Final purification by flash column chromatography (silica gel, 80% hexane, 20% ethyl acetate) yielded the desired compound (34%) as a colorless oil.

c). To a solution of potassium tert-butoxide (705 mg, 6.33 mmol) in anhydrous THF (25 mL) at 0° C., bis(2,2,2-trifluoroethyl)phosphite (1.00 mL, 6.33 mmol) was added. 2-bromo-N,N-dimethylacetamide (12.66 mmol) was then added by syringe. Upon completion of the addition step, the reaction was allowed to proceed for one hour with monitoring by TLC. The reaction was then quenched with a saturated solution of aqueous ammonium chloride (20 mL). The aqueous phase was extracted with diethyl ether (3×20 mL). The combined organic extracts were washed with water (3×20 mL) and with a saturated sodium chloride solution (1×20 mL). The solvent was removed by rotary evaporation and the crude material was further concentrated under oil pump vacuum. The final product was purified by column chromatography (silica gel, 2:1 hexanes/ethyl acetate) yielding the desired compound (41%).

(ii) From bis-(2,2,2-trifluoroethyl)phosphonoacetic acid.

a). Via Acyl Chloride

A solution of bis-(2,2,2-trifluoroethyl)phosphonoacetic acid (0.1 mol) and thionyl chloride (100 ml) was stirred for 3-5 h at room temperature. 200 ml of dichloroethane were added and the excess of thionyl chloride was distilled off together with some solvent, this process was performed 2-3 times to remove completely the thionyl chloride. The concentrated dichloroethane solution of crude acyl chloride was added to a mixture of 100 mL H$_2$O, 40% aq. HNMe$_2$, and Na$_2$CO$_3$ at −5 to 5° C. and the resulting mixture was stirred at room temperature for 2-3 h. The organic phase was separated and the water phase was extracted with dichloroethane (3×30 ml). The combined organic extracts were washed with water (3×20 mL) and with a saturated sodium chloride solution (1×20 mL). After the removal of the solvent by rotary evaporation, the crude material was further concentrated under oil pump vacuum. Distillation of residue gave bis(2,2,2-trifluoroethyl) 2-(dimethylamino)-2-oxoethylphosphonate with 78% yield.

b). Via Active Ester

Bis-(2,2,2-trifluoroethyl)phosphonoacetic acid (0.07 mol) was dissolved in 100 ml of ethyl acetate. To this solution 5.6 g of pyridine (0.07 mol) were added, followed by 20.4 g (0.093 mol) of Boc anhydride. The mixture was stirred for 15 min and anhydrous dimethylamine (0.07 mol) was added. The mixture was stirred overnight. The mixture was stirred for 1 h at 5° C., and worked-up. Following distillation bis(2,2,2-trifluoroethyl) 2-(dimethylamino)-2-oxoethylphosphonate was obtained in 80% yield.

Phosphonate Ester Interchange

Bis(2,2,2-trifluoroethyl) 2-(dimethylamino)-2-oxoethylphosphonate was prepared by Phosphonate Ester Interchange as described for analogous reactions [Still, W. C.; Gennari, C. *Tetrahedron Lett.* 1983, 24, 4405-4408; Bodnarchuk, N. D.; Malovik, V. V.; Derkach; G. I. *Zh. Obshch. Khim.* 1970, 40, 1210, the contents of each of which is incorporated by reference herein]:

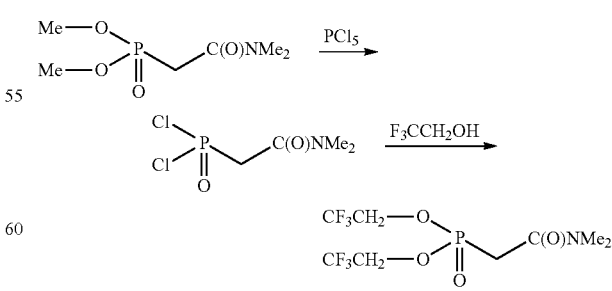

Bis(phenyl)-2-(dimethylamino)-2-oxoethylphosphonate and bis(o-tolyl)-2-(dimethylamino)-2-oxoethylphosphonate were prepared according to the above procedures.

Example 2

Preparation of [1-(Dimethylcarbamoyl)ethyl]phosphonic acid bis-(2,2,2-trifluoroethyl) ester (15)

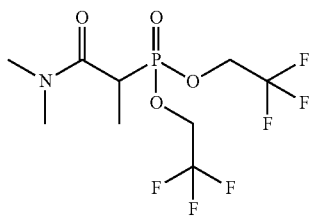 [SMILES: CC(C(=O)N(C)C)P(=O)(OCC(F)(F)F)OCC(F)(F)F]

a). Bis(2,2,2-trifluoroethyl) 2-(dimethylamino)-2-oxoethylphosphonate (14) (4.7 g, 14.2 mmol) was slowly added to a solution of tert-BuOK (1.9 g, 17.0 mmol) in THF (20 ml) at 0° C. under nitrogen atmosphere. The mixture was stirred at these conditions for 30 minutes methyl iodide (4.42 ml, 70.9 mmol) was slowly added keeping the temperature at 0° C. After stirring at room temperature for 14 h under nitrogen atmosphere, the reaction mixture was treated with saturated aqueous solution of $NH_4Cl$ and then extracted with AcOEt (50 ml×3). The extracts were concentrated t to give an oily residue, which was purified by vacuum distillation or column chromatography on silica gel [n-hexane/AcOEt (2:1)] to afford 3.2 g of the wanted compound(65%) as a colorless oil.

$^1$H-NMR (400 MHz, $CDCl_3$) δ: 1.52 (dd, J=19.8 Hz, J=7.3 Hz, 3H), 3.48 (s, 6H), 3.87 (1H, dq, J=22.9 Hz, J=7.3 Hz), 4.40 (dq, J=8.3, 8.2 Hz, 4H); $^{13}$C NMR (100 MHz, $CDCl_3$) δ: 12.4 (d, J=7.7 Hz, $CH_3CH$) 34.4 (s, $NMe_2$), 62.0 (dq, J=38.3, 6.1 Hz, $CF_3CH_2$), 64.4 (qd, J=37.6, 5.0 Hz, CH), 122.4 (dq, J=277.4, 8.4 Hz, $CF_3$), 169.6 (C=O)

$^{31}$P NMR ($CDCl_3$) δ: 24.67.

EI-MS calculated for $C_9H_{14}F_6NO_4P$ MW 345.18. found m/z 345.06;

Anal. calculated $C_9H_{14}F_6NO_4P$: C, 31.32; H, 4.09; F, 33.02; N, 4.06; P, 8.97. Found: C, 31.26; H, 3.85; F, 33.0; N, 3.86; P, 8.67.

The product of vacuum distillation may contain 2-3% of dimethyl-impurity, formed by over alkylation of bis(2,2,2-trifluoroethyl) 2-(dimethylamino)-2-oxoethylphosphonate. This impurity does not participate in further reaction and [1-(dimethylcarbamoyl)ethyl]phosphonic acid bis-(2,2,2-trifluoroethyl) ester can be used without additional purification.

b). A flame-dried 1-L three-necked round-bottom flask equipped with a Teflon-coated magnetic stir bar, thermometer, rubber septum and argon inlet was charged with 51.0 mL (128 mmol, 2.41 eq.) of a 2.5 M solution of n-butyllithium in hexanes and 40 mL of THF under argon atmosphere, and cooled to an internal temperature of −20±3° C. using a dry ice-isopropanol-water bath for 20 min. Into a separate flame-dried 100-mL one-necked round-bottom flask equipped with a rubber septum and argon inlet 29.2 mL (139 mmol, 2.64 eq.) of 1,1,1,3,3,3-hexamethyldisilazane (HMDS) and 40 mL of THF were charged under argon atmosphere. The mixture was stirred and transferred dropwise via cannula to the above n-butyllithium solution over 20 min while maintaining the internal temperature below −15° C. The 100-mL flask was then rinsed with THF (2×10 mL), and the THF washes cannulated to the larger flask over 5 min. The resulting clear solution was stirred at −20±3° C. for 20 minutes, and cooled to an internal temperature of −75° C. with a dry ice-acetone bath. A separate 100-mL one-necked round-bottomed flask equipped with a rubber septum and argon inlet was then charged with 14.5 g (52.9 mmol, 1.00 eq.) of ethylphosphonic acid bis-(2,2,2-trifluoroethyl) ester, 7.84 g (72.9 mmol, 1.38 eq.) dimethylcarbamoyl chloride and 50 mL of THF, and transferred dropwise via cannula to the above lithium HMDS solution over 30 minutes while maintaining the internal temperature below −68° C. The smaller flask was rinsed with THF (2×10 mL), and the THF washes transferred by cannula to the larger flask over 5 min. The resulting pale yellow solution was re-cooled to −75° C. and stirred for 2.5 h, then slowly acidified over 5 min with 130 mL of a 1.0 M solution of HCl, and gradually warmed to an internal temperature of 0° C. over 30 min. The solution was diluted with 100 mL of distilled water, and transferred to a 1-L separatory funnel. The flask was rinsed with diethyl ether (3×50 mL), the combined washes were transferred to the funnel, shaken, the layers separated, and the aqueous layer extracted with dichloromethane (4×100 mL). The combined organic phases were dried ($MgSO_4$), filtered, and concentrated by rotary evaporation (35° C., 20 mmHg) to afford 19 g of a yellow oil, which could be used for further reactions or purified by distillation or column chromatography, as follows: the yellow oil was loaded onto a 80-mm diameter column, wet-packed (4:1 hexanes:ethyl acetate) with 450 grams (25 cm) of silica gel, and sequentially eluted with a gradient of hexanes and ethyl acetate (2 L of 2:1, 2 L of 1:1, 1 L of 1:2). The desired product was collected in fractions of 75-mL volume, concentrated by rotary evaporation (35° C., 20 mmHg), and dried under vacuum (25° C., 0.01 mmHg) until a constant mass is obtained. The above described procedure afforded [1-(dimethylcarbamoyl)ethyl]phosphonic acid bis-(2,2,2-trifluoroethyl) ester as a clear slightly yellow oil with 82-88% yield.

Example 3

Preparation of methyl 3-(3-methoxyphenyl)-2-methylpent-2-enoate (16, R'=$OCH_3$)

a). HWE Reaction with $Sn(OSO_2CF_3)_2$

A solution of Ethyl-2-[Bis(2,2,2-trifluoroethyl)phosphonopropionate (1.24 mmol) in anhydrous dichloroethane (5 ml) was added to a suspension of $Sn(OSO_2CF_3)_2$ (0.6 g, 1.48 mmol) in anhydrous dichloroethane (10 ml) and stirred at room temperature for min under argon. After adding N-ethylpiperidine (0.15 g, 1.36 mmol), the mixture was 10 stirred at 0° C. for 1 h under argon atmosphere, and then heated to reflux. 3-methoxy phenyl ethyl ketone (11) (0.14 g, 0.88 mmol) was slowly added to the refluxing solution. Following reflux under TLC or GC control for completion of the reaction (18-20 h) under argon atmosphere, the reaction mixture was poured into water (10 ml) and then extracted with methylene chloride or chloroform (20 ml×3). Hexane (50 ml) was added to the organic extracts, and the mixture was submitted to filtration through a silica gel short column [n-hexane/$CHCl_3$ (2:1)]. The filtrate was evaporated in vacuum to afford a crude product, which could be used for the next step or purified by column chromatography on silica gel [n-hexane/MTBE (10:0.5)] to afford the desired compound as a colorless oil with 75% yield.

b). HWE Reaction with NaH

To a suspension of NaH (60% in oil, 66 mg, 1.65 mmol) in anhydrous THF (15 ml) was added a solution of Ethyl-2-[Bis(2,2,2-trifluoroethyl)phosphonopropionate (1.24 mmol) in anhydrous THF (10 ml) at 0° C. The mixture was stirred at 0° C. for 1 h under argon atmosphere, and then heated to reflux.

3-methoxy phenyl ethyl ketone (11) (0.16 g, 1.0 mmol) was added to the refluxing solution.

Following reflux under TLC or GC control for completion of the reaction (18-20 h) under inert atmosphere, 5% HCl (15 ml) was added and then extracted with MTBE (20 ml×3). The extracts were concentrated to give a crude product (E:Z=10: 90), which can be directly used for the next step or purified by column chromatography on silica gel [n-hexane/MTBE (10: 0.5)] to afford the E-isomer and Z-isomer as a pale yellow oil and a colorless oil, respectively.

Methyl (Z)-2-Methyl-3-(p-methoxyphenyl)-2-pentenoate: $^1$H-NMR (400 MHz, CDCl$_3$) δ: 1.04 (3H, t, J=7.5 Hz), 2.02 (3H, s), 2.38 (2H, q, J=7.5 Hz), 3.51 (3H, s), 3.82 (3H, s), 6.40 (d, 1H), 6.87-6.92 (2H, m), 7.22 (1H, t)

EI-MS calculated for $C_{14}H_{18}O_3$ MW 234.1256. found m/z 234.1249 (M1);

Anal. calculated for $C_{14}H_{18}O_3$: C, 71.77; H, 7.74. Found: C, 71.74; H, 7.62.

Methyl (E)-2-Methyl-3-(p-methoxyphenyl)-2-pentenoate: $^1$H-NMR (400 MHz, CDCl$_3$) δ: 0.96 (3H, t, J=7.5 Hz), 1.73 (3H, s), 2.59 (2H, q, J=7.5 Hz), 3.78 (3H, s), 3.82 (3H, s), 6.42 (d, 1H), 6.87-6.92 (2H, m), 7.22 (1H, t)

EI-MS calculated for $C_{14}H_{18}O_3$ MW 234.1256. found m/z 234.1245 (M1).

Anal. Calculated for $C_{14}H_{18}O_3$: C, 71.77; H, 7.74. Found: C, 71.68; H, 7.72.

Example 4

Preparation of 3-(3-methoxyphenyl)-N,N,2-trimethylpent-2-en amide (17)

a). Reaction with Sn(OSO$_2$CF$_3$)$_2$

The Z-isomer was prepared according to EXAMPLE 3 (a) from bis(2,2,2-trifluoroethyl)-1-(dimethylamino)-1-oxopropan-2-ylphosphonate (15) and 3-methoxyphenyl ethyl ketone (11) with 75% yield and >98.5% purity. (Z)-3-(3-methoxyphenyl)-N,N,2-trimethylpent-2-enamide.

$^1$HNMR (400 MHz, CDCl$_3$) δ: 1.06 (3H, t, J=7.5 Hz), 2.20 (2H, q, J=7.5 Hz), 2.43 (3H, s); 3.18 (3H, s), 3.83 (3H, s), 6.40 (d, 1H), 6.84-6.90 (2H, m), 7.20 (1H, t)

EI-MS calculated for $C_{15}H_{21}NO_2$ MW 247.33. found m/z 247.32 (M1).

Anal. Calculated for $C_{15}H_{21}NO_2$: C, 72.84; H, 8.56; N, 5.66. Found: C, 72.80; H, 8.58; N, 5.46.

The same results were obtained with (diarylphosphono) propanoates (ArO)$_2$P(O)CH(CH$_3$)C(O)NMe$_2$:
Ar=Ph, Z-isomer (72% yield and 98.6% purity)=o-MeC$_6$H$_4$, Z-isomer (76% yield and 99.0% purity).

b). Reaction with NaH 3-(3-methoxyphenyl)-N,N,2-trimethylpent-2-en amide was prepared according to EXAMPLE 3 (a) as a mixture of E- and Z-isomers (7:93).

With bis(ethyl)-1-(dimethylamino)-1-oxopropan-2-ylphosphonate instead of bis(2,2,2-trifluoroethyl)-1-(dimethylamino)-1-oxopropan-2-ylphosphonate, 3-(3-methoxyphenyl)-N,N,2-trimethylpent-2-en amide was prepared according to EXAMPLE 3(a) (NaH, THF, 55° C.) as a mixture of E- and Z-isomers (28:72).

c). From methyl 3-(3-methoxyphenyl)-2-methylpent-2-enoate.

To a solution of crude methyl 3-(3-methoxyphenyl)-2-methylpent-2-enoate (1.25 mmol) in ethanol (20 ml) was added 10% aqueous sodium hydroxide (30 g). After stirring at room temperature for 5 h, the reaction mixture was evaporated. The resultant residue was washed with hexane (10 ml).

To the water layer were added diethyl ether (50 ml) and 6N hydrochloric acid (200 ml). The mixture was extracted with diethyl ether (3×30 ml). The ethereal layers were dried over anhydrous magnesium sulfate and evaporated to give the corresponding crude acid (yield 88%). To a stirred solution of the crude acid in anhydrous benzene or dichloroethane (10 ml) was added distilled thionyl chloride (0.8 ml, 11.0 mmol) at 0° C. under an inert atmosphere. After 5 h reflux and the removal of the volatiles in vacuo, the residue was diluted with distilled tetrahydrofuran (10 ml) and to this solution 50% aqueous dimethylamine (1.63 g, 11.0 mmol) was added at 0° C. After stirring at 0° C. for 2 h, the reaction was quenched with 3N hydrochloric acid (10 ml) and extracted with diethyl ether (3×20 ml). The ethereal layers were dried over anhydrous magnesium sulfate and evaporated. The yield was 64%. The compound could be used directly in the next step or be purified by silica gel column chromatography (hexane/ethyl acetate, 5:1).

Example 5

Preparation of (2R,3R)-methyl 3-(3-methoxyphenyl)-2-methylpentanoate (18)

a). By reduction of Z-methyl 3-(3-methoxyphenyl)-2-methylpent-2-enoate (16)

Unsaturated ester (16) (1 mmol) was hydrogenated (15 atm H$_2$, 20° C., 7 h) in propan-2-ol (15 ml) in the presence of Raney nickel (0.3 g). The filtration and evaporation of the solvent left crude methyl erythro-methyl 3-(3-methoxyphenyl)-2-methylpentanoate ((2R,3R)-methyl 3-(3-methoxyphenyl)-2-methylpentanoate) (18). $^1$HNMR (400 MHz, CDCl$_3$) δ: 0.82 (3H, t, J=8.0 Hz), 1.20 (3H, dd, J=8.0 Hz), 1.52 (2H, m), 2.80 (2H, m); 3.40 (1H, m), 3.68 (3H, s), 3.83 (3H, s), 6.81-6.86 (2H, m), 7.08 (1H, s), 7.26 (1H, m).

EI-MS calculated for $C_{14}H_{20}O_3$ MW 236.14. found m/z 236.14 (M1).

Anal. Calculated for $C_{14}H_{20}O_3$: C, 71.16; H, 8.53. Found: C, 71.00; H, 8.48.

b). The same result was obtained by hydrogenation, using palladium 10% on activated carbon (20 bar, room temperature).

c). Hydrogenation of Z-methyl 3-(3-methoxyphenyl)-2-methylpent-2-enoate (16), using Ru-based catalyst.

The catalyst was prepared from Ru(COD)(methallyl)$_2$, C3-TunaPhos and HBF$_4$.Me$_2$O, according to [J. AM. CHEM. SOC. 2003, 125, 9570-9571, the contents of which are incorporated by reference herein], was used in situ by dissolving in degassed dried MeOH or EtOH (3 mL), and the solution was directly used for hydrogenation. To the catalyst solution was added a substrate (Ru:P*:HBF$_4$:substrate=1:1:2:20). The resulting mixture was transferred into an autoclave and charged with 50 atm of H$_2$ pressure. The autoclave was stirred at room temperature for 18-20 h. The reaction solution was then evaporated and the residue was passed through a short silica gel plug to remove the catalyst. The resulting hydrogenation product was then directly analyzed by chiral GC (chiralselect 1000 or gamma dex 225) to determine the enantiomeric excess. The desired compound was obtained with 99% conversion and 95 ee. THF, methylene chloride, or toluene were also used as solvents.

d). Hydrogenation of Z-methyl 3-(3-methoxyphenyl)-2-methylpent-2-enoate (16), using Rh-based catalyst.

Rhodium catalyst was prepared in situ by mixing RhCl (NBD), AgBF$_4$, and chiral ligand (21a) in a ratio of 1:1:1.3 and 5 mol % of triethylamine in a 90:10 mixture of THF and methanol, according to [Tetrahedron Letters, Vol. 29, No. 46, pp 5969-5972, 1988, the contents of which are incorporated by reference herein].

Hydrogenation of Z-methyl 3-(3-methoxyphenyl)-2-methylpent-2-enoate (16) (1.0 mmol) was carried out in the presence of 0.5 mol % of a rhodium catalyst at room temperature and 50 atm of initial hydrogen pressure. The hydrogenation was completed in 30 h. The reaction solution was then evaporated and the residue was passed through a short silica gel plug to remove the catalyst to give a quantitative yield of the product. The enantiomeric excess was determined to be 98.5% by HPLC analysis with a chiral stationary phase column. Use of methanol as solvent in place of the mixed solvent increased the rate of hydrogenation, though the stereoselectivity was a little lower (94.0% ee).

e). Hydrogenation of mixture E- and Z-methyl 3-(3-methoxyphenyl)-2-methylpent-2-enoate (16), using Rh-based catalyst.

Hydrogenation of a mixture of isomers (E:Z=7:93) from Example 4 (b), using the same rhodium catalyst gave the mixture of (S)- and (R)-isomers in ratio 6:94.

f). Hydrogenation of Z-methyl 3-(3-methoxyphenyl)-2-methylpent-2-enoate (16), using iridium catalyst.

Irridium catalyst (22d) was prepared according to [Adv. Synth. Catal. 2008, 350, 174-178, the contents of which are incorporated by reference herein].

A 50-mL autoclave equipped with a magnetic stir bar was filled with a substrate (0.1 mmol) and an iridium catalyst (1 mol %) dissolved in dichloromethane (0.5 mL). The autoclave was pressurized to 50 bar with $H_2$ and the solution was stirred at room temperature for 2-5 h. The pressure was released slowly and the solvent was evaporated. The residue was passed through a short silica gel plug to remove the catalyst. The filtrate was directly analyzed by GC to determine the conversion and ee. The conversion was 99% with 87% ee.

Example 6

Preparation of (2R,3R)-3-(3-methoxyphenyl)-N,N,2-trimethylpentanamide (19) by hydrogenation of (Z)-3-(3-methoxyphenyl)-N,N,2-trimethylpent-2-enamide (17)

Hydrogenation was performed according to Example 5 (a).

(2R,3R)-3-(3-methoxyphenyl)-N,N,2-trimethylpentanamide (19) was obtained with 97% ee, $^1$HNMR (400 MHz, CDCl$_3$) δ: 0.76 (3H, t, J=8.0 Hz), 1.18 (3H, dd, J=8.0 Hz), 1.50 (2H, m), 2.68 (2H, m); 3.40 (1H, m), 3.47 (6H, s), 3.80 (3H, s), 6.80-6.86 (2H, m), 7.08 (1H, s), 7.24 (1H, m).

EI-MS calculated for $C_{15}H_{23}NO_2$ MW 249.17. found ink 249.17 (M1).

Anal. Calculated for $C_{15}H_{23}NO_2$: C, 72.25; H, 9.30; N, 5.62. Found: C, 72.0; H, 9.48; N, 5.28.

b). Hydrogenation, Using Ruthenium Based Catalyst

Hydrogenation was performed according to Example 5 (c), affording desired compound with 89% ee.

c). Hydrogenation, Using Rhodium Based Catalyst.

Hydrogenation was performed according to Example 5 (d), affording desired compound with 92% ee.

Example 7

Preparation of (2R,3R)-3-(3-methoxyphenyl)-N,N,2-trimethylpentanamide (19) from (2R,3R)-methyl 3-(3-methoxyphenyl)-2-methylpentanoate (18)

Transformation of (2R,3R)-methyl 3-(3-methoxyphenyl)-2-methylpentanoate to (2R,3R)-3-(3-methoxyphenyl)-N,N,2-trimethylpentanamide was performed according to Example 4 (c).

Example 8

Preparation of (2R,3R)-3-(3-methoxyphenyl)-N,N,2-trimethylpentan-1-amine (7) as hydrochloride Boron trifluoride diethyl etherate (3.5 mL, 30 mmol) was dissolved in 25 ml of dry tetrahydrofuran and stirred at (−10)-(−5)° C. Sodium borohydride (1.1 g, 30 mmol) was added portion wise to this solution, and the mixture stirred at room temperature for 1-2 h. After cooling to 0-5° C., (2R,3R)-3-(3-methoxyphenyl)-N,N,2-trimethylpentanamide (1.25 g, 5 mmol) was added and the mixture was stirred at room temperature and monitored by TLC. Following reaction completion, the mixture was concentrated under reduced pressure to yield solids, which were dissolved in 100 ml of 5% hydrochloric acid, and the hydrochloric acid phase was subsequently washed twice with 50 ml diisopropylether. The hydrochloric acid phase was subsequently made alkaline with concentrated sodium hydroxide solution whilst cooling in an ice bath, and was solvent-extracted twice with 50 ml dichloromethane. Subsequent to drying the combined organic phases over sodium sulphate, the solvent was distilled off under vacuum and the remaining residue (5.2 g) was taken up in 2-butanone. Hydrogen chloride was then added and the hydrochloride of (2R,3R)-3-(3-methoxyphenyl)-N,N,2-trimethylpentan-1-amine (75%) crystallized out; m.p.: 162-164° C.; $[\alpha]_D^{RT}$=−25.0 (c=0.95; methanol).

Example 9

Preparation of Tapentadol

Preparation of tapentadol was performed according to EP-A-0693475, the contents of which are incorporated by reference herein. 4.3 g (15 mmole) of (2R,3R)-3-(3-methoxyphenyl)-N,N,2-trimethylpentan-1-amine hydrochloride was added to 100 ml of concentrated hydrobromic acid. The mixture was then heated under reflux for two hours. After cooling to room temperature the reaction mixture was concentrated under reduced pressure. The residue was treated with concentrated sodium hydrogen carbonate solution until pH=8.0-8.5. After extracting with dichloromethane (50 ml×2) the combined organic phases were dried over sodium sulphate. Dichloromethane was then distilled off under reduced pressure and the residue (4 g) was taken up in 2-butanone. Following the addition of hydrogen chloride, 3.8 g of tapentadol hydrochloride (98% theoretical) crystallized out; m.p.: 190-194° C.; $[\alpha]_D^{RT}$=−24.2° (c=1.10; methanol).

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

What is claimed is:

1. A process for the preparation of a compound of formula (A):

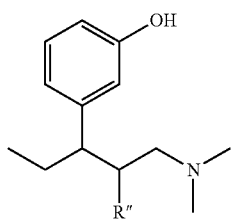

(A)

or stereoisomers, pharmaceutically acceptable salts, or combination thereof, comprising steps (a), (b1), (c1), (d) and (e); or (a), (b2), (c2), (d) and (e):
  a) a Horner-Wadsworth-Emmons (HWE) reaction between 1-(3-methoxy-phenyl)-propan-1-one and a phosphonate compound of formula (I) to obtain a compound of formula (II):

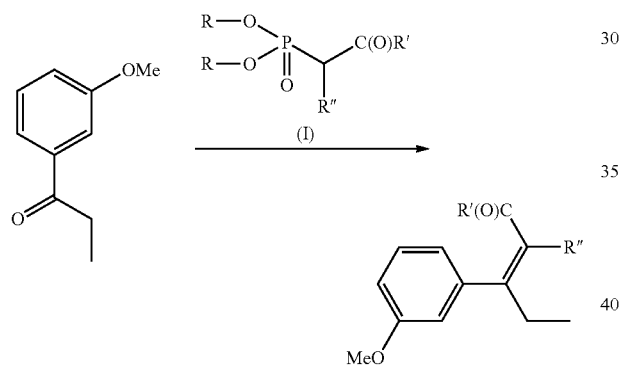

wherein each R is independently alkyl or aryl which is optionally substituted with an electron withdrawing group;
R' is (i) —$NR^1R^2$ wherein $R^1$ and $R^2$ are each alkyl; (ii) —$OR^3$ wherein $R^3$ is alkyl, aryl or alkylaryl; or (iii) a functional group which can be converted to an amine group; and
R" is H, alkyl, aryl, heteroalkyl, heteroaryl, alkylaryl or cycloalkyl;
b1) and c1): hydrogenating compound (II) to obtain the compound of formula (III):

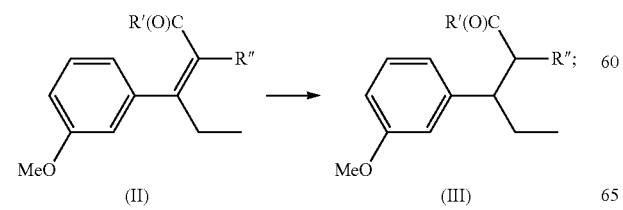

and
optionally, when R' is other than $NMe_2$, converting the compound of formula (III) to a compound of formula (IV):

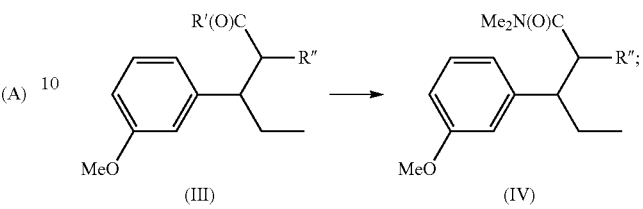

or
b2) and c2) optionally, when R' is other than $NMe_2$, converting the compound of formula (II) to a compound of formula (V):

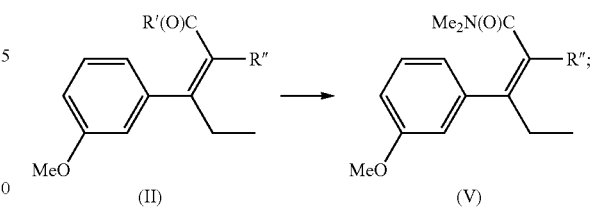

and
hydrogenating compound (V) to obtain the compound of formula (IV):

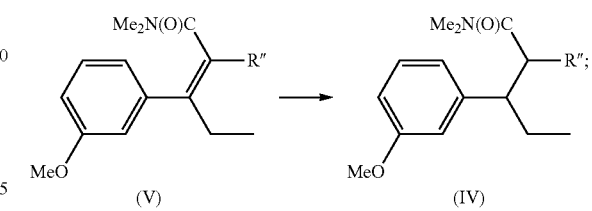

d) reducing the resultant compound of formula (IV) obtained in steps (c1) or (c2) to a compound of formula (VI):

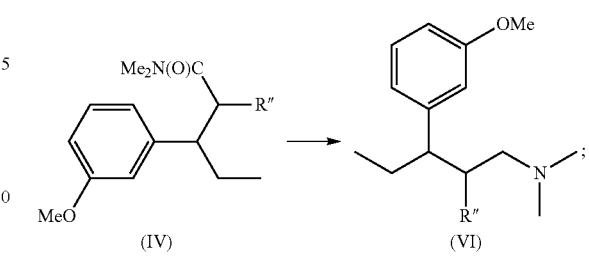

and
e) converting the compound of formula (VI) to a compound of formula (A):

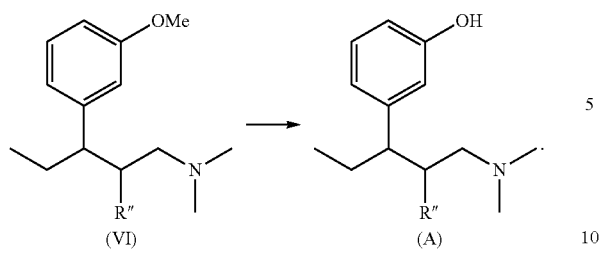

2. The process according to claim 1, wherein R is 2,2,2-trifluoroethyl, phenyl or o-tolyl.

3. The process according to claim 1, wherein R' is NMe$_2$.

4. The process according to claim 1, wherein R" is methyl and the compound of formula (A) is 3-[3-(dimethylamino)-1-ethyl-2-methylpropyl]phenol, or stereoisomers, pharmaceutically acceptable salts, or combination thereof.

5. The process according to claim 4, wherein the compound is 3-[(1R,2R)-3-(dimethylamino)-1-ethyl-2-methylpropyl]phenol (Tapentadol) or pharmaceutically acceptable salts thereof, wherein the process comprises the steps of (a), (b1), (c1), (d) and (e), or (a), (b2), (c2), (d) and (e):

a) a Horner-Wadsworth-Emmons (HWE) reaction between 1-(3-methoxy-phenyl)-propan-1-one and a phosphonate compound of formula (I-a) to obtain a compound of formula (II-a):

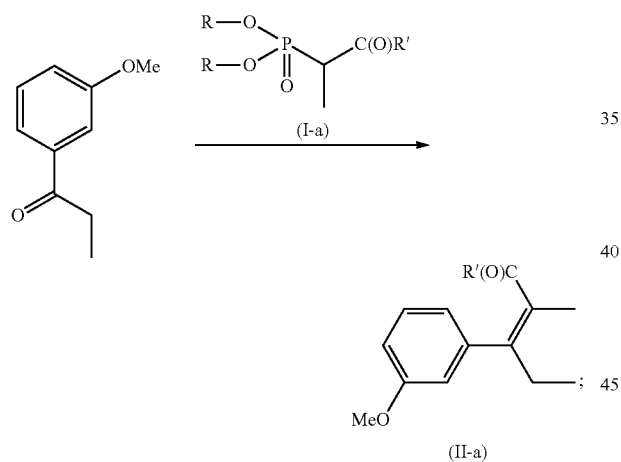

b1) and c1) hydrogenating compound (II-a) to obtain a compound of formula (III-a):

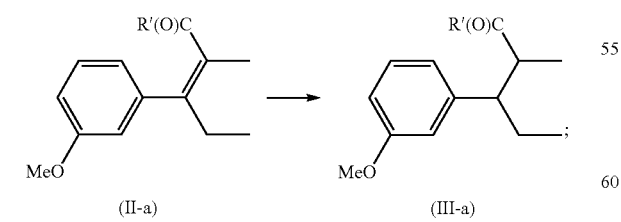

and optionally, when R' is other than NMe$_2$, converting the compound of formula (III-a) to a compound of formula (IV-a):

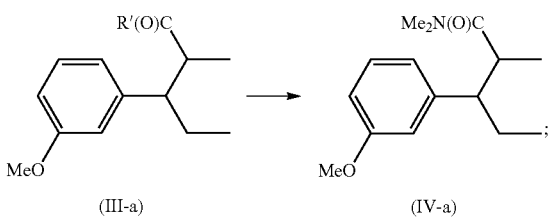

or b2) and c2) optionally, when R' is other than NMe$_2$, converting the compound of formula (II-a) to a compound of formula (V-a):

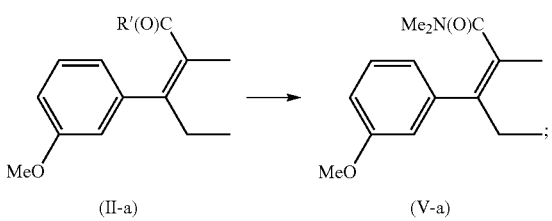

and hydrogenating compound (V-a) to obtain the compound of formula (IV-a):

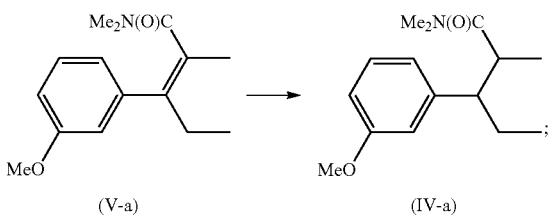

d) reducing the compound of formula (IV-a) obtained by step (c1) or (c2) to 3-(3-methoxyphenyl)-N,N,2-trimethylpentan-1-amine of formula (VI-a):

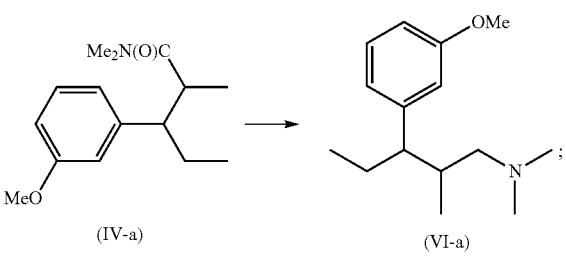

and e) converting 3-(3-methoxyphenyl)-N,N,2-trimethylpentan-1-amine to 3-[3-(dimethylamino)-1-ethyl-2-methylpropyl]phenol or stereoisomers, pharmaceutically acceptable salts or combination thereof,

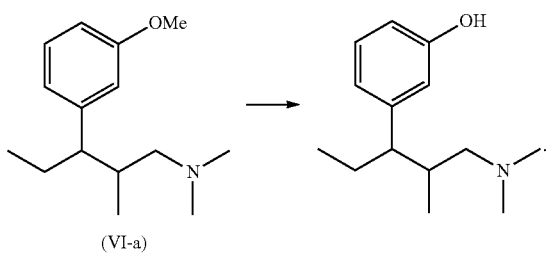 [SMILES: CCC(c1cccc(OC)c1)C(C)CN(C)C ; CCC(c1cccc(O)c1)C(C)CN(C)C]

(VI-a)

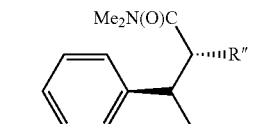

(IV)

(III-a)

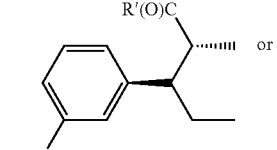

or

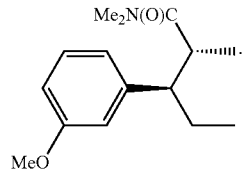

(IV-a)

6. The process according to claim 1, comprising the steps (a), (b1), (c1), (d) and (e).

7. The process according to claim 1, comprising the steps (a), (b2), (c2), (d) and (e).

8. The process according to claim 1, wherein in step (a) the HWE reaction is performed in the presence of an inorganic or an organic base, wherein
the inorganic base is selected from alkali metal and alkaline earth hydrides and alcoholates;
the organic base is a tertiary amine selected from DNU, DBN and diisopropylethylamine;
or wherein step (a) is performed in the presence of an organic base in combination with alkali metal or alkaline earth metal halogenides.

9. The process according to claim 1, wherein in step (a) the compound of formula (II) or (II-a) is formed as a Z-isomer or as a mixture of E- and Z-isomers.

10. The process according to claim 1, wherein in step (b1) or (c2) the hydrogenation is carried out in the presence of a catalyst under hydrogen atmosphere in an organic solvent, wherein the catalyst is selected from the group consisting of copper, zinc, nickel, ruthenium, palladium, platinum, rhodium, and their oxides, Raney nickel and Pd/C.

11. The process according to claim 10, wherein the catalyst is used in combination with a support selected from the group consisting of silica, alumina, silica-alumina, titania, diatomaceous earth, kaolin, activated carbon, carbon, graphite, zeolite, montmorillonite, clays and alkaline earth metal silicates.

12. The process according to claim 11, wherein the catalyst is a complex of transition metals selected form the group consisting of rhodium, ruthenium, iridium, platinum, titanium, zirconium and palladium.

13. The process according to claim 12, wherein the catalyst is associated with a chiral ligand.

14. The process according to claim 1, wherein the product of formula (III) or (III-a) obtained in step (b1), or the product of formula (IV) or (IV-a) obtained in steps (c1) or (c2) is in the form of a racemic mixture.

15. The process according to claim 1, wherein the compound of formula (III) or (M-a) obtained in step (b1), or the compound of formula (IV) or (IV-a) obtained in steps (c1) or (c2) is in an optically active form, as a threo-isomer which is represented by any of the structures:

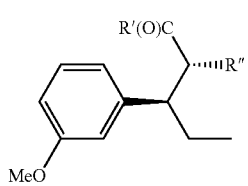

(III)

16. The process according to claim 1, wherein R' is other than NMe$_2$, and step (c1) or (b2) are performed, or wherein R' is NMe$_2$, and step (c1) or (b2) are not performed.

17. The process according to claim 1, wherein in step (d) the reduction of the compound of formula (IV) or (IV-a) is carried out with a reducing agent selected from the group consisting of borane and its complex with dimethylsulfide, pyridine or triethylamine; lithium borohydride or sodium borohydride in the presence of a Lewis acid wherein the Lewis acid is selected from boron trifluoride diethyl ether complex, and aluminum-, titanium- or cobalt-chlorides, or in the presence of trimethylchlorosilane or phosphorus oxychloride; and an aluminum hydride selected from AlH$_3$ and its complex with amines, LiAlH$_4$, sodium bis(2-methoxyethoxy)aluminum hydride (Red-Al) and diisobutylaluminum hydride.

18. The process according to claim 1, further comprising the step of converting the compound of formula (A) or its precursor of formula (VI) into a pharmaceutically acceptable salt thereof.

19. The process according to claim 18, wherein the compound of formula (A) is Tapentadol, and the process further comprises the step of converting Tapentadol or its precursor of formula (VI-a) into its hydrochloride salt.

20. A phosphonate compound represented by structure of formula (I-a):

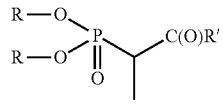

(I-a)

wherein each R is independently alkyl or aryl which is optionally substituted with an electron withdrawing group, or wherein R is 2,2,2-trifluoroethyl, phenyl or o-tolyl, and R' is N(CH$_3$)$_2$.

21. A compound represented by the structure of formula (II) or (III):

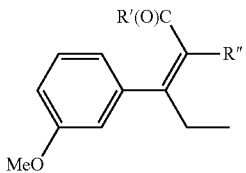
(II)

wherein R' is —NR¹R² wherein R¹ and R² are each alkyl; and R" is alkyl, aryl, heteroalkyl, heteroaryl, alkylaryl or cycloalkyl;

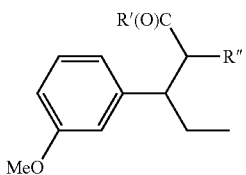
(III)

wherein R' is (i) —NR¹R² wherein R¹ and R² are each alkyl; (ii) —OR³ wherein R³ is alkyl, aryl or alkylaryl; or (iii) a functional group which can be converted to an amine group; and R" is alkyl, aryl, heteroalkyl, heteroaryl, alkylaryl or cycloalkyl.

22. The compound of formula (II) according to claim 21, wherein the compound exists as the Z-isomer, or as a mixture of Z- and E-isomers.

23. The compound of formula (II) according to claim 21, which is represented by the structure of formula (II-a) (V) or (Va):

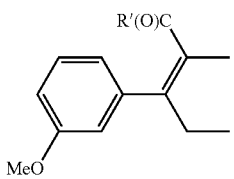
(II-a)

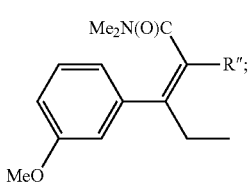
(V)

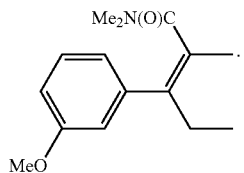
(V-a)

24. The compound of formula (III) according to claim 21, wherein the compound exists in optically active form as a threo-isomer, which is represented by the structure:

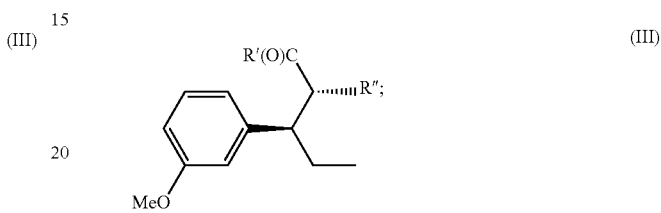
(III)

or
wherein the compound exists as a racemic mixture.

25. The compound of formula (III) according to claim 21, wherein the compound is represented by the structure of formula (III-a), (IV) or (IVa), including stereoisomers thereof:

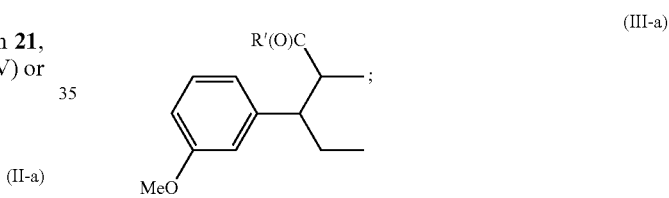
(III-a)

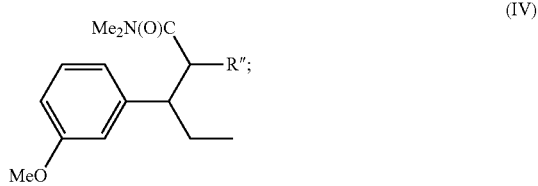
(IV)

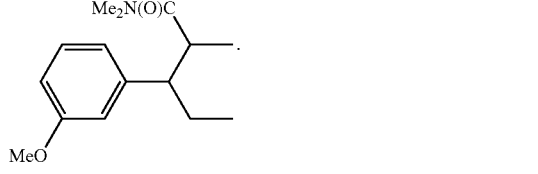
(IV-a)

* * * * *